US008491475B2

(12) United States Patent
Ogasawara

(10) Patent No.: US 8,491,475 B2
(45) Date of Patent: Jul. 23, 2013

(54) ULTRASONIC DIAGNOSTIC APPARATUS, ULTRASONIC DIAGNOSTIC METHOD, AND IMAGING PROCESSING PROGRAM FOR ULTRASONIC DIAGNOSTIC APPARATUS

(75) Inventor: Yoichi Ogasawara, Nasushiobara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 753 days.

(21) Appl. No.: 11/668,914

(22) Filed: Jan. 30, 2007

(65) Prior Publication Data
US 2007/0239005 A1 Oct. 11, 2007

(30) Foreign Application Priority Data

Jan. 30, 2006 (JP) .................................. 2006-021077

(51) Int. Cl.
*A61B 8/00* (2006.01)
(52) U.S. Cl.
USPC ........... 600/437; 600/407; 600/443; 600/447; 382/131; 345/8
(58) Field of Classification Search
USPC ................ 600/437, 443, 447; 382/131; 345/8
See application file for complete search history.

(56) References Cited

U.S. PATENT DOCUMENTS

| 5,301,674 A * | 4/1994 | Erikson et al. ................ 600/447 |
| 6,033,072 A * | 3/2000 | Ono et al. ...................... 351/208 |
| 6,757,416 B2 * | 6/2004 | Kleiman et al. ............... 382/131 |
| 6,847,336 B1 * | 1/2005 | Lemelson et al. ................. 345/8 |
| 2004/0212695 A1 * | 10/2004 | Stavely et al. ............. 348/231.3 |
| 2005/0195277 A1 * | 9/2005 | Yamasaki ........................ 348/61 |
| 2005/0256407 A1 * | 11/2005 | Hamada ........................ 600/447 |

FOREIGN PATENT DOCUMENTS

| JP | 61-172552 | 8/1986 |
| JP | 7-128705 A | 5/1995 |
| JP | 9-18775 | 1/1997 |
| JP | 2001-70293 | 3/2001 |
| JP | 2001-224594 | 8/2001 |
| JP | 2002-238892 | 8/2002 |

OTHER PUBLICATIONS

Office Action issued Apr. 26, 2011, in Japanese Patent Application No. 2006-021077.
Japanese Office Action Issued Oct. 2, 2012 in Patent Application No. 2006-021077.

* cited by examiner

*Primary Examiner* — Unsu Jung
*Assistant Examiner* — Joseph M Santos
(74) *Attorney, Agent, or Firm* — Oblon, Spivak, McClelland, Maier & Neustadt, L.L.P.

(57) ABSTRACT

An ultrasonic diagnostic apparatus including a line-of-sight position data obtaining unit that obtains current line-of-sight position data of the operator from a line-of-sight position input unit, and a setting condition change unit that changes an area that is set based on the line-of-sight position data. Further, the setting condition change unit refers to focal point position setting condition database and changes a focal point position that is set based on the set area data. A control unit shifts the focal point position to a transmission unit and a reception unit. Furthermore, the setting condition change unit refers to the image quality setting condition database and changes a set image quality setting condition to an optimal image quality setting condition based on the set area data.

14 Claims, 17 Drawing Sheets

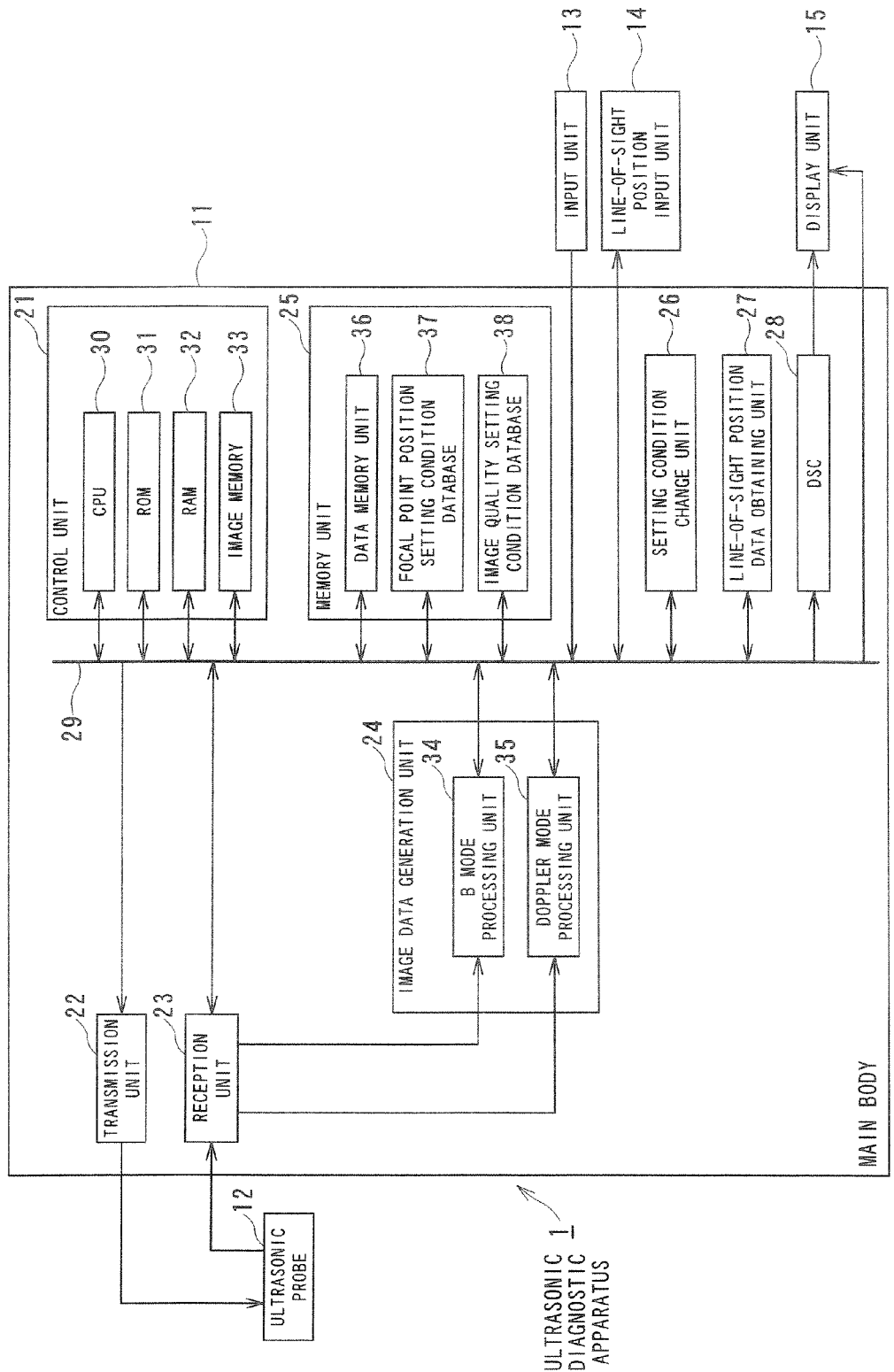
F I G. 1

| AREA | TRANSMISSION WAVEFORM OF ULTRASONIC WAVE | TRANSMISSION FREQUENCY | TRANSMISSION WAVE NUMBER | RECEPTION FREQUENCY | ACOUSTIC POWER LEVEL OF ULTRASONIC WAVE |
|---|---|---|---|---|---|
| AREA 1 | b1 | c1 | d1 | e1 | f1 |
| AREA 2 | b2 | c2 | d2 | e2 | f2 |
| AREA 3 | b3 | c3 | d3 | e3 | f3 |
| AREA 4 | b4 | c4 | d4 | e4 | f4 |
| AREA 5 | b5 | c5 | d5 | e5 | f5 |

IMAGE QUALITY SETTING CONDITION DATABASE

F I G. 16

ULTRASONIC DIAGNOSTIC APPARATUS, ULTRASONIC DIAGNOSTIC METHOD, AND IMAGING PROCESSING PROGRAM FOR ULTRASONIC DIAGNOSTIC APPARATUS

BACKGROUND OF THE INVENTION

1. Field of the Invention

The present invention relates to an ultrasonic diagnostic apparatus, an ultrasonic diagnostic method, and an imaging processing program for the ultrasonic diagnostic apparatus. In particular, the invention relates to an ultrasonic diagnostic apparatus, an ultrasonic diagnostic method, and an imaging processing program for the ultrasonic diagnostic apparatus allowing the improvement of an operability.

2. Description of the Related Art

An ultrasonic diagnostic apparatus is a medical diagnostic apparatus for displaying an image of in vivo information. The ultrasonic diagnostic apparatus is inexpensive as compared with other medical diagnostic apparatuses such as an X-ray diagnostic apparatus and X-ray CT apparatus, and does not cause a patient (hereinafter referred to as "subject body") to suffer from exposure. Furthermore, the ultrasonic diagnostic apparatus is noninvasive and can perform real-time measurement, and thus this apparatus is used as a useful diagnostic apparatus. The application scope of the ultrasonic diagnostic apparatus is wide. The ultrasonic diagnostic apparatus is applied to circulatory organs such as heart, abdominal parts such as liver and kidney, peripheral blood vessels, cerebral blood vessels, and the like.

Incidentally, when a panel of the apparatus is operated while a target area of the subject body is scanned by using the ultrasonic diagnostic apparatus, a doctor, a technician, or the like (hereinafter referred to as "operator") needs to twist or bend its body while the hands are fixed so that a scan cross-section image appropriate to the diagnosis is displayed. As a result, a large number of operators complain of shoulder stiffness and lower-back pain. In Europe, it is reported that 80% of operators working for the check-up with use of the ultrasonic diagnostic apparatus report any form of body aches, and 20% of these operators retire due to physical injuries. Many of such reports are filed up, and among those reports, it is mentioned that the design itself of the ultrasonic diagnostic apparatus is a main cause, and some reports have concluded that the design has a problem in terms of human engineering.

As one of the problems in design for this ultrasonic diagnostic apparatus, when operating the ultrasonic diagnostic apparatus, the operator cannot use both hands during the operation. In view of the above, in order to solve such a problem, a method is proposed with which an operator uses a foot switch and the operator performs an input by the foot.

Also, from the viewpoint of human engineering, a method is proposed with which setting for an image mode and an image quality condition for the ultrasonic diagnostic apparatus is performed by voice input.

Furthermore, a method is proposed with which a remote control system is used, and a check-up complicated procedure based on the ultrasonic diagnostic apparatus is combined with a macro control, thereby operating the ultrasonic diagnostic apparatus with a simple operation in a composite approach.

In addition, for a general surgery, a method is proposed with which an operator uses an operating microscope (optical device) to perform an input on the basis of a line-of-sight. In particular, a line-of-sight automatic tracking method is proposed which the optical device is caused to automatically track the line-of-sight gazing at the observation target area with respect to a displacement between the line-of-sight of the operator and an observation target area without any operation by the operator, and the desired observation target area is shifted to the field-of-view center area.

However, with the method of performing the input by the foot with use of the foot switch, even if both the hands are occupied during the operation, the operator can perform the input by the foot with use of the foot switch, but in the first place, the input relies on the foot, so there is still a problem in that the operability of the ultrasonic diagnostic apparatus is not good.

Also, with the method of performing the input by the foot with use of the foot switch, because the operator performs the input by the foot, the foot of the operator is at a place not relatively easy to see, and the like, any complicated operations cannot be provided. Thus, there is a problem in that the operations provided to the foot switch are limited to simple operations such as ON/OFF control on scan freeze and outputting of a screen image.

Moreover, with the method of performing the setting on the image more and the image quality for the ultrasonic diagnostic apparatus on the basis of the voice input, the voice recognition rate of the voice input is still not perfect, and if the voice input is used, there is a problem in that the operator can perform either the setting on the image more and the image quality for the ultrasonic diagnostic apparatus or communication with a subject body.

Then, with the method of operating the ultrasonic diagnostic apparatus with the simple operation in a composite approach while a remote control system is used and the complicated procedure for the check-up based on the ultrasonic diagnostic apparatus is combined with the macro control, the operator can perform the operation on the ultrasonic diagnostic apparatus with the simple operation in a composite approach, but there is a problem in that the input to the remote control still needs to be conducted through a hand of the operator.

Furthermore, with a method proposed in Japanese Unexamined Patent Application Publication No. 61-172552, the optical device is caused to automatically track the line-of-sight gazing at the observation target area with respect to the displacement between the line-of-sight of the operator and the observation target area without any operation by the operator, and the desired observation target area is shifted to the field-of-view center area, but only the position of the observation target area can be shifted, so there is a problem in that the method cannot be applied to an ultrasonic diagnostic apparatus that requires various inputs by the operator.

SUMMARY OF THE INVENTION

The present invention was made in the view of the circumstances encouraged in the prior art mentioned above, and it is an object to provide an ultrasonic diagnostic apparatus, an ultrasonic diagnostic method, and an imaging processing program for the ultrasonic diagnostic apparatus allowing the improvement of an operability.

In order to solve the above-mentioned problems, an ultrasonic diagnostic apparatus according to an aspect of the present invention includes: an image data generation unit vibrating a plurality of ultrasonic transducers to transmit ultrasonic waves, receiving and converting reflected waves reflected from a subject body by the ultrasonic transducers into a reception signal, and generating image data on the basis of the reception signal; a line-of-sight position data obtaining unit obtaining line-of-sight position data that is data on the line-of-sight position of an operator; and a setting condition change unit changing a setting condition used when the image data is generated by the image data generation unit, on the basis of the line-of-sight position data obtained by the line-of-sight position data obtaining unit.

In order to solve the above-mentioned problems, an ultrasonic diagnostic method according to an aspect of the present invention includes: an image data generation step of vibrating a plurality of ultrasonic transducers to transmit ultrasonic waves, receiving and converting reflected waves reflected from a subject body by the ultrasonic transducers into a reception signal, and generating image data on the basis of the reception signal; a line-of-sight position data obtaining step of obtaining line-of-sight position data that is data on the line-of-sight position of an operator; and a setting condition change step of changing a setting condition used when the image data is generated in the image data generation step, on the basis of the line-of-sight position data obtained in the line-of-sight position data obtaining step.

In order to solve the above-mentioned problems, an imaging processing program for an ultrasonic diagnostic apparatus according to an aspect of the present invention causes a computer to execute a procedure that includes: an image data generation step of vibrating a plurality of ultrasonic transducers to transmit ultrasonic waves, receiving and converting reflected waves reflected from a subject body by the ultrasonic transducers into a reception signal, and generating image data on the basis of the reception signal; a line-of-sight position data obtaining step of obtaining line-of-sight position data that is data on the line-of-sight position of an operator; and a setting condition change step of changing a setting condition used when the image data is generated in the image data generation step, on the basis of the line-of-sight position data obtained in the line-of-sight position data obtaining step.

In order to solve the above-mentioned problems, an ultrasonic diagnostic apparatus according to an aspect of the present invention includes: an image data generation unit vibrating a plurality of ultrasonic transducers to transmit ultrasonic waves, receiving and converting reflected waves reflected from a subject body by the ultrasonic transducers into a reception signal, and generating image data on the basis of the reception signal; a head area position data obtaining unit obtaining head area position data that is data related to a head area of an operator; and a setting condition change unit changing a setting condition used when the image data is generated by the image data generation unit, on the basis of the head area position data obtained by the head area position data obtaining unit.

In order to solve the above-mentioned problems, an ultrasonic diagnostic method according to an aspect of the present invention includes an image data generation step of vibrating a plurality of ultrasonic transducers to transmit ultrasonic waves, receiving and converting reflected waves reflected from a subject body by the ultrasonic transducers into a reception signal, and generating image data on the basis of the reception signal; a head area position data obtaining step of obtaining head area position data that is data related to a head area of an operator; and a setting condition change step of changing a setting condition used when the image data is generated in the image data generation step, on the basis of the head area position data obtained in the head area position data obtaining step.

In order to solve the above-mentioned problems, an imaging processing program for an ultrasonic diagnostic apparatus according to an aspect of the present invention causes a computer to execute a procedure that includes: an image data generation step of vibrating a plurality of ultrasonic transducers to transmit ultrasonic waves, receiving and converting reflected waves reflected from a subject body by the ultrasonic transducers into a reception signal, and generating image data on the basis of the reception signal; a head area position data obtaining step of obtaining head area position data that is data related to a head area of an operator; and a setting condition change step of changing a setting condition used when the image data is generated in the image data generation step, on the basis of the head area position data obtained in the head area position data obtaining step.

In the ultrasonic diagnostic apparatus, the ultrasonic diagnostic method, and the imaging processing program for an ultrasonic diagnostic apparatus according to an aspect of the present invention, the plurality of ultrasonic transducers are vibrated to the transmit ultrasonic waves, the reflected waves reflected from a subject body are received and converted by the ultrasonic transducers into a reception signal, the image data is generated on the basis of the reception signal, the line-of-sight position data that is data on the line-of-sight position of the operator is obtained, and the setting condition used when the image data is generated is changed on the basis of the line-of-sight position data.

In the ultrasonic diagnostic apparatus, the ultrasonic diagnostic method, and the imaging processing program for an ultrasonic diagnostic apparatus according to an aspect of the present invention, the plurality of ultrasonic transducers are vibrated to the transmit ultrasonic waves, the reflected waves reflected from a subject body are received and converted by the ultrasonic transducers into a reception signal, the image data is generated on the basis of the reception signal, the head area position data that is data related to the head area of the operator, and the setting condition used when the image data is generated is changed on the basis of the line-of-sight position data.

The nature and further characteristic features of the present invention will be made more clear from the following descriptions made with reference to the accompanying drawings.

BRIEF DESCRIPTION OF THE DRAWINGS

In the accompanying drawings:

FIG. 1 is a block diagram of an internal construction of an ultrasonic diagnostic apparatus according to the present invention;

FIG. 16 shows an example of an image quality setting condition database stored in the memory unit of the main body in FIG. 1;

DESCRIPTION OF THE PREFERRED EMBODIMENTS

Figure 2:
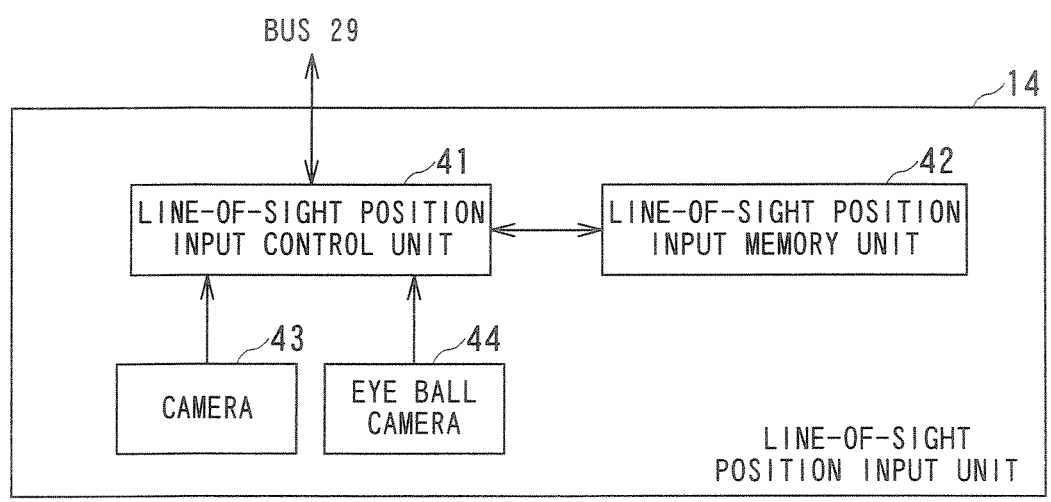
FIG. 2 is a block diagram of an internal construction of a line-of-sight position input unit in FIG. 1.

With reference to drawings, embodiments of the invention will be described below.

FIG. 1 shows an internal construction of an ultrasonic diagnostic apparatus 1 according to the present invention.

The ultrasonic diagnostic apparatus 1 is constructed by a main body 11, an ultrasonic probe 12 connected to the main body 11 via an electric cable (not shown), an input unit 13, a line-of-sight position input unit 14, and a display unit 15.

As shown in FIG. 1, the main body 11 of the ultrasonic diagnostic apparatus 1 is composed of a control unit 21, a transmission unit 22, a reception unit 23, an image data generation unit 24, a memory unit 25, a setting condition change unit 26, a line-of-sight position data obtaining unit 27, and a DSC (Digital Scan Converter) 28.

It should be noted that the control unit 21, the transmission unit 22, the reception unit 23, the image data generation unit 24, the memory unit 25, the setting condition change unit 26, the line-of-sight position data obtaining unit 27, and the DSC 28 are connected to one another in the main body 11 of the ultrasonic diagnostic apparatus 1 via a bus 29.

The control unit 21 includes a CPU (Central Processing Unit) 30, a ROM (Read Only Memory) 31, a RAM (Random Access Memory) 32, and an image memory 33. The CPU 30 performs processing in accordance with a program stored in the ROM 31 or various application programs loaded from the memory unit 25 to the RAM 32, generates and outputs various control signals to a component in order to centrally control the drive of the ultrasonic diagnostic apparatus 1.

In addition, the RAM 32 appropriately stores necessary data for the CPU 30 to execute various processing The image memory 33 obtains B mode image data and Doppler mode image data (for instance, spectrum Doppler mode image data, color Doppler mode image data, or the like) supplied from the image data generation unit 24 and stores the thus obtained B mode image data and the Doppler mode image data. As a result, for example, after the diagnosis, the operator makes the ultrasonic diagnostic apparatus 1 be capable to read the image data stored during the diagnosis and display the data via the DSC 28 on the display unit 15 as a still image or a moving image.

Also, the image memory 33 appropriately stores various image data such as raw data like an output signal (RF signal) supplied from the reception unit 23 and the image data obtained via a network (not shown), and supplies the data to the respective units when necessary.

It should be noted that instead of using the CPU 30, an MPU (Micro Processing Unit) or the like may be used.

The transmission unit 22 is composed of a rate pulse generator, a transmission delay circuit, and a pulsar (all of which are not shown in the drawing). The rate pulse generator generates a rate pulse for determining a pulse repetition frequency of an ultrasonic pulse entering the inside of the subject body on the basis of the control signal supplied from the control unit 21 to be supplied to the transmission delay circuit. Also, the transmission delay circuit is a delay circuit for setting the focal point position and the deflection angle of the ultrasonic beam at the time of the transmission unit. In order that the focal point position and the deflection angle of the ultrasonic beam at the time of the transmission become a predetermined focal point position and a predetermined deflection angle, based on the control signal supplied from the control unit 21, a delay time is added to the rate pulse supplied from the rate pulse generator to be supplied to the pulsar. Furthermore, the pulsar is a driver circuit for generating a high pressure pulse for driving an ultrasonic transducer. On the basis of the rate pulse supplied from the transmission delay circuit, a high pressure pulse for driving an ultrasonic transducer is generated, and the generated high pressure pulse is output to the ultrasonic probe 12.

It should be noted that in accordance with the control of the control unit 21, the transmission unit 22 can immediately change the delay time added to the rate pulse, a transmission frequency, a transmission drive voltage, and the like. In particular, in order that the transmission unit 22 can immediately change the transmission drive voltage, the transmission unit 22 is provided, for example, with a transmission circuit of a linear amplifier type, a circuit that can electrically switch a plurality of power source units, etc.

The reception unit 23 is composed, for example, of a preamplifier, an A/D converter, a reception delay circuit, and an adder circuit (all of which are not shown in the drawing). The preamplifier obtains a reception signal based on the reflected wave of the ultrasonic pulse entering the subject body from the ultrasonic probe 12, amplifies the thus obtained reception signal to a predetermined level, and supplies the amplified reception signal to the A/D converter. The A/D converter converts the reception signal supplied from the preamplifier from the analog signal to the digital signal to be supplied to the reception delay circuit.

The reception delay circuit gives a delay time necessary to determine the reception directivity to the reception signal after the A/D conversion that has been supplied from the A/D converter on the basis of the control signal supplied from the control unit 21 (a delay time corresponding to a difference in propagation time of the ultrasonic waves from the focal point position of the respective ultrasonic transducers) to be supplied to the adder circuit. The adder circuit adds the reception signals from the respective ultrasonic transducers supplied from the reception delay circuit and supplies the added reception signal to the image data generation unit 24. It should be noted that the addition by the adder circuit emphasizes the reflection component from the direction corresponding to the reception directivity of the reception signal.

The image data generation unit 24 is composed, for example, of a B mode processing unit 34 and a Doppler mode processing unit 35. The B mode processing unit 34 is composed of a logarithmic amplifier, an envelope detection circuit, and a TGC (Time Gain Control) circuit (all of which are not shown in the drawing), and performs the following processing on the basis of the control signal supplied from the control unit 21.

That is, the logarithmic amplifier of the B mode processing unit 34 performs logarithmic amplification on the reception signal supplied from the reception unit 23 and supplies the reception signal after the logarithmic amplification to the envelope detection circuit. The envelope detection circuit is a circuit for removing a ultrasonic frequency component and only detecting an amplitude. The envelope detection circuit detects the envelope with respect to the reception signal supplied from the logarithmic amplifier and supplies the detected reception signal to the TGC circuit. The TGC circuit adjusts the intensity of the reception signal supplied from the envelope detection circuit so that the final images have a uniform luminance and supplies the B mode image data after the adjustment to the image memory 33 or the memory unit 25 of the control unit 21. The B mode image data stored in the image memory 33 or the memory unit 25 of the control unit 21 is supplied via the DSC 28 to the display unit 15, and thereafter displayed as the B mode image data in which the intensity of the reception signal is represented by the luminance.

The Doppler mode processing unit 35 is further composed of a spectrum Doppler mode process unit and a color Doppler mode process unit (all of which are not shown in the drawing).

The spectrum Doppler mode process unit of the Doppler mode processing unit 35 is composed of a Doppler shift signal detector (not shown) for detecting a Doppler shift signal from the reception signal supplied from the reception unit 23 and an analysis unit (not shown) for detecting a spectrum distribution of the Doppler shift signal detected by the Doppler shift signal detector.

The Doppler shift signal detection unit is composed of a reference signal generator, π/2 phase shifter, a mixer, an LPF (Low Pass Filter), and the like (all of which are not shown in the drawing). The Doppler shift signal detection unit mainly performs an orthogonal phase detector and the like with respect to the reception signal supplied from the reception unit 23 and supplies the detected Doppler shift signal to the analysis unit.

The analysis unit is composed of an FFT (Fast Fourier Transform) analyzer, a computing unit, and the like. The FFT analyzer performs the FFT analysis on the Doppler shift signal supplied from the Doppler shift signal detection unit at a predetermined width with a predetermined depth corresponding to the position of a sample maker as the center. The computing unit calculates the center frequency, the dispersion, or the like with respect to the frequency spectrum from the FFT analyzer and supplies the spectrum Doppler mode image data generated through the calculation to the image memory 33 or the memory unit 25 of the control unit 21. The spectrum Doppler mode image data stored in the image memory 33 or the memory unit 25 of the control unit 21 is supplied via a spectrum Doppler drawing processing unit (not shown) to the display unit 15, and thereafter displayed as a spectrum Doppler mode image which represents the distribution of the frequency spectrum contained in the reception signal.

On the other hand, the color Doppler mode process unit of the Doppler mode processing unit 35 is composed of the Doppler shift signal detector (not shown) for detecting the Doppler shift signal from the reception signal that is supplied from the reception unit 23 and an extraction calculation unit (not shown) for extracting blood stream information such as an average speed, dispersion, power of the blood stream from the Doppler shift signal detected by the Doppler shift signal detector. It should be noted that the Doppler shift signal detection unit not shown of the color Doppler mode process unit has the similar construction as that of the Doppler shift signal detection unit not shown of the spectrum Doppler mode process unit and the description will be omitted to avoid the repetition.

The extraction calculation unit is composed of an MTI filter (Moving Target Indication Filter), an autocorrelator, an average speed computing unit, a distributed computing unit, a power calculator, and the like (all of which are not shown in the drawing). The MTI filter performs removal of an unnecessary fixed reflector (for instance, a blood vessel wall, a cardiac wall, or the like) on the Doppler shift signal supplied from the Doppler shift signal processing unit and supplies the Doppler shift signal from which the fixed reflected waves are removed to the autocorrelator. The autocorrelator performs a frequency analysis at a large number of points of the Doppler shift signal supplied from the MTI filter after the removal of the fixed reflected waves in real time to be supplied to the average speed computing unit, the distributed computing unit, and the power calculator.

The average speed computing unit, the distributed computing unit, and the power calculator respectively calculate the average speed, the dispersion, and the power of the blood current and supplies the color Doppler mode image data generated through the calculation to the image memory 33 or the memory unit 25 of the control unit 21. The color Doppler mode image data stored in the image memory 33 or the memory unit 25 of the control unit 21 is supplied via the DSC 28 to the display unit 15 and thereafter displayed as a color Doppler mode image indicating the blood current information such as the average speed, the dispersion, and the power of the blood current.

The memory unit 25 includes, for example, an HDD (Hard Disc Drive) and a non-volatile memory (all of which are not shown in the drawing), and is structured by a data memory unit 36, a focal point position setting condition database 37, and an image quality setting condition database 38. The data memory unit 36 stores a control program for executing a scan sequence, an image generation and display processing, a difference image generation processing, a luminance value holding calculation processing, a control program for executing superposition display or the like, various data groups related to diagnosis information (a patient ID, findings of the doctor, and the like), a diagnosis protocol, a transmission and reception condition of the ultrasonic wave, a calculation condition of the calculation processing. Also, the data memory unit 36 stores, if necessary, various image data supplied from the image memory 33 of the control unit 21. The data memory unit 36 can transfer various data, if necessary, via an interface unit (not shown) to an external device (not shown).

Furthermore, the data memory unit 36 stores, for example, the line-of-sight position data that is data on the current line-of-sight position of the operator, the focal point position data that is data on the current focal point position of the ultrasonic beam at the time of transmission, and the like, and appropriately supplies the stored data in accordance with the control from the control unit 21 to the respective units of the main body 11.

An area to which the line-of-sight position of the operator belongs and a focal point position of the ultrasonic beam at the time of the transmission are previously registered in association with each other in the focal point position setting condition database 37, and the focal point position setting condition database 37 is appropriately supplied to the setting condition change unit 26 in accordance with the control from the control unit 21. A plurality of areas to which the line-of-sight position of the operator belongs and the setting conditions related to various image qualities (for example, a transmission waveform of an ultrasonic wave, a transmission frequency, a transmission wave number, and the like) are previously registered in association with each other in the image quality setting condition database 38, and the image quality setting condition database 38 is appropriately supplied to the setting condition change unit 26 in accordance with the control from the control unit 21.

The setting condition change unit 26 refers to the databases respectively managed by the focal point position setting condition database 37 and the image quality setting condition database 38 of the memory unit 25, and on the basis of the current line-of-sight position data of the operator supplied from the line-of-sight position data obtaining unit 27 and various data supplied from the data memory unit 36 of the memory unit 25, changes the area to which the current line-of-sight position of the operator belongs as well as the focal point position and the image quality setting condition. Also, the setting condition change unit 26 supplies the area data that is data on the changed area to which the current line-of-sight position of the operator belongs, the focal point position data that is data on the changed focal point position, and the changed image quality setting condition data to the data memory unit 36 of the memory unit 25.

The line-of-sight position data obtaining unit 27 obtains the line-of-sight position data of the operator supplied from the line-of-sight position input unit 14, and supplies the thus obtained line-of-sight position data to the control unit 21 and the memory unit 25.

The DSC 28 reads out the B mode image data, the Doppler mode image data, and the like supplied from the image memory 33 of the control unit 21, converts the read B mode image data, the read Doppler mode image data, and the like from a scanning line signal train of an ultrasonic scan to a scanning line signal train of a video format, and subjects the resultant to a predetermined image processing and a calculation processing to be supplied to the display unit 15.

The ultrasonic probe 12 is connected to the main body 11 via an electric cable (not shown). The ultrasonic probe 12 is an ultrasonic transducer for performing transmission and reception for the ultrasonic wave by contacting its front surface with the surface of the subject body and has minute ultrasonic transducers arranged in one-dimensional array or two-dimensional matrix at its distal end part. The ultrasonic transducer is formed of an electro-acoustic transducer as a piezoelectric vibrator. At the front side of the ultrasonic transducer, a matching layer for efficiently propagating the ultrasonic wave is provided. At the back side of the ultrasonic transducers, a packing material for preventing the rearward propagation of the ultrasonic wave is provided.

The ultrasonic probe 12 converts an electric pulse incident from the transmission unit of the main body 11 into an ultrasonic pulse (transmission ultrasonic wave) at the time of the transmission and converts a reflected wave reflected by the subject body into an electric signal at the time of the reception to be output to the main body 11. It should be noted that a part of the transmitted ultrasonic waves inside the subject body is reflected by a boundary phase between organs having different acoustic impedances in the subject body or a tissue. Also, when reflected by a moving blood current, a surface of the cardiac wall, or the like, the transmitted ultrasonic wave receives a frequency shift due to Doppler effect.

The input unit 13 is connected via an electric cable to the main body 11, a display panel (not shown) for inputting various inputs of the operator on an operation panel, and an input device such as a track ball, a variety of operation switches, a range of buttons, a mouse, and a keyboard. The input unit 13 is used when the operator inputs various data such as the patient information, measurement parameters, and physical parameters.

The line-of-sight position input unit 14 appropriately supplies, in accordance with the control from the control unit 21 of the main body 11, the line-of-sight position data that is data on the line-of-sight position of the operator to the line-of-sight position data obtaining unit 27 of the main body 11. It should be noted that of course the line-of-sight position input unit 14 may perform exchange of data with respect to the main body 11 by way of wireless communication using infrared lays, Blutooth (registered trademark) or the like.

The display unit 15 is connected via a cable to the DSC 28 of the main body 11 and is provided with an LCD (Liquid Crystal Display) and a CRT (Cathode Ray Tube) which are not shown in the drawing. The display unit 15 obtains spectrum Doppler image data after a drawing processing from a spectrum Doppler drawing processing unit (not shown) and also obtains the B mode image data, the color Doppler mode image data, and the like from the DSC 28 converted from the scanning line signal train of the ultrasonic scan to the scanning line signal train of the video format, and the spectrum Doppler image based on the thus obtained spectrum Doppler image data, the B mode image based on the B mode image data, and the color Doppler mode image based on color Doppler mode image data, and the like are displayed on an LCD or a CRT which are not shown in the drawing.

Also, the display unit 15 displays, in accordance with the control of the control unit 21, various dialogs (a line-of-sight input start dialog 54, a focal point position shift dialog 61, a image quality setting condition change dialog 63, or a image quality setting condition change dialog 65 that will be described with reference to FIG. 9, 15, 17, or 20).

FIG. 2 shows an internal structure of the line-of-sight position input unit 14 in FIG. 1.

As shown in FIG. 2, the line-of-sight position input unit 14 is structured by a line-of-sight position input control unit 41, a line-of-sight position input memory unit 42, a camera 43, and an eye ball camera 44. It should be noted that the line-of-sight position input unit 14 is designed in advance so as to be mounted to the head area of the operator and so that the camera 43 can pick up an image displayed on the display unit 15 and also the eye ball camera 44 can capture an image of the eye balls of the operator.

Figure 5:
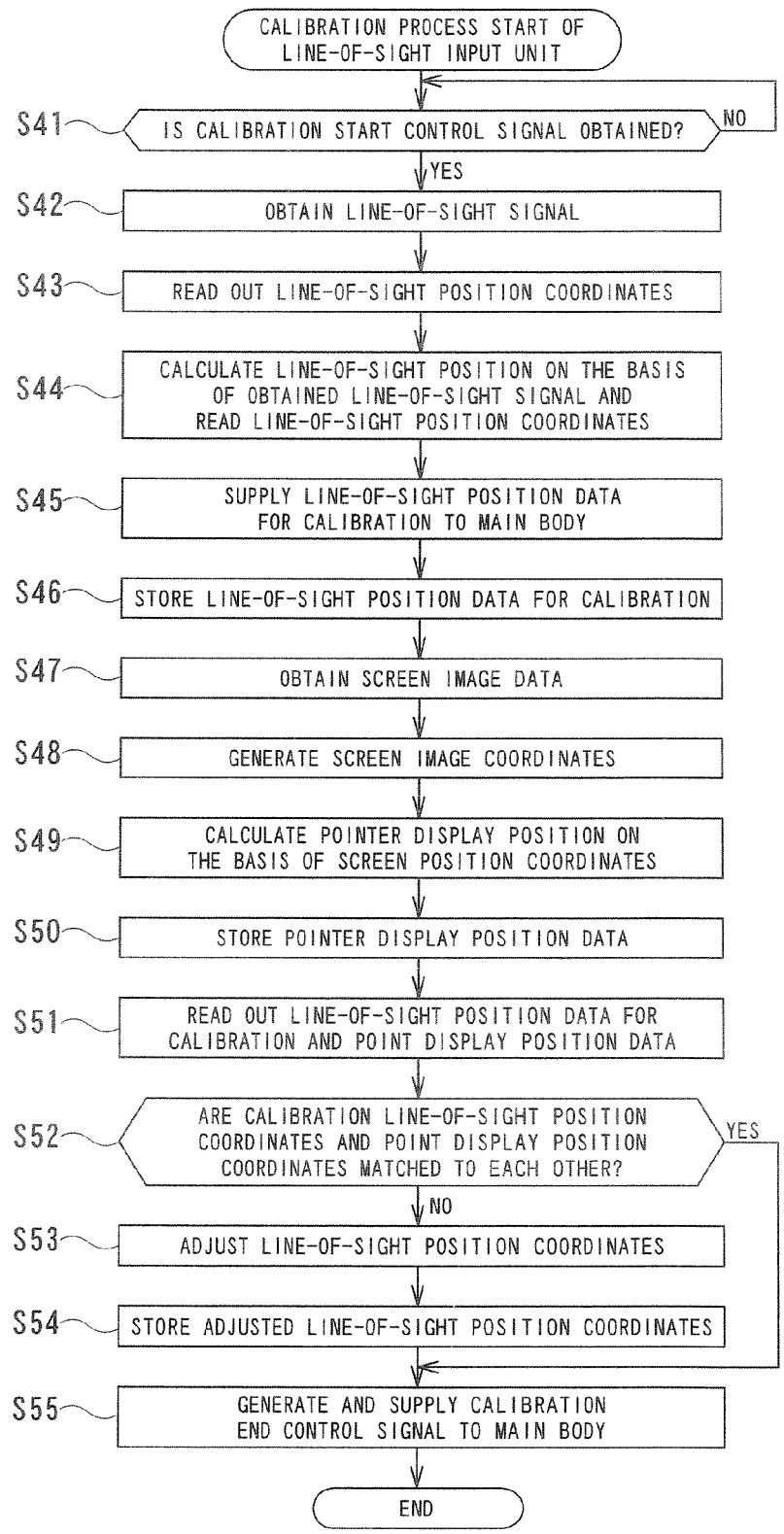
FIG. 5 is a flowchart for describing calibration processing of the line-of-sight position input unit in FIG. 1.

The line-of-sight position input control unit 41 obtains a calibration start control signal supplied from the control unit 21 of the main body 11, and starts a calibration process (as will be described later while referring to the flowchart of FIG. 5) on the basis of the thus obtained calibration start control signal. The line-of-sight position input control unit 41 generates a calibration end control signal when the calibration process is ended, and supplies the signal to the main body 11.

Figure 10:
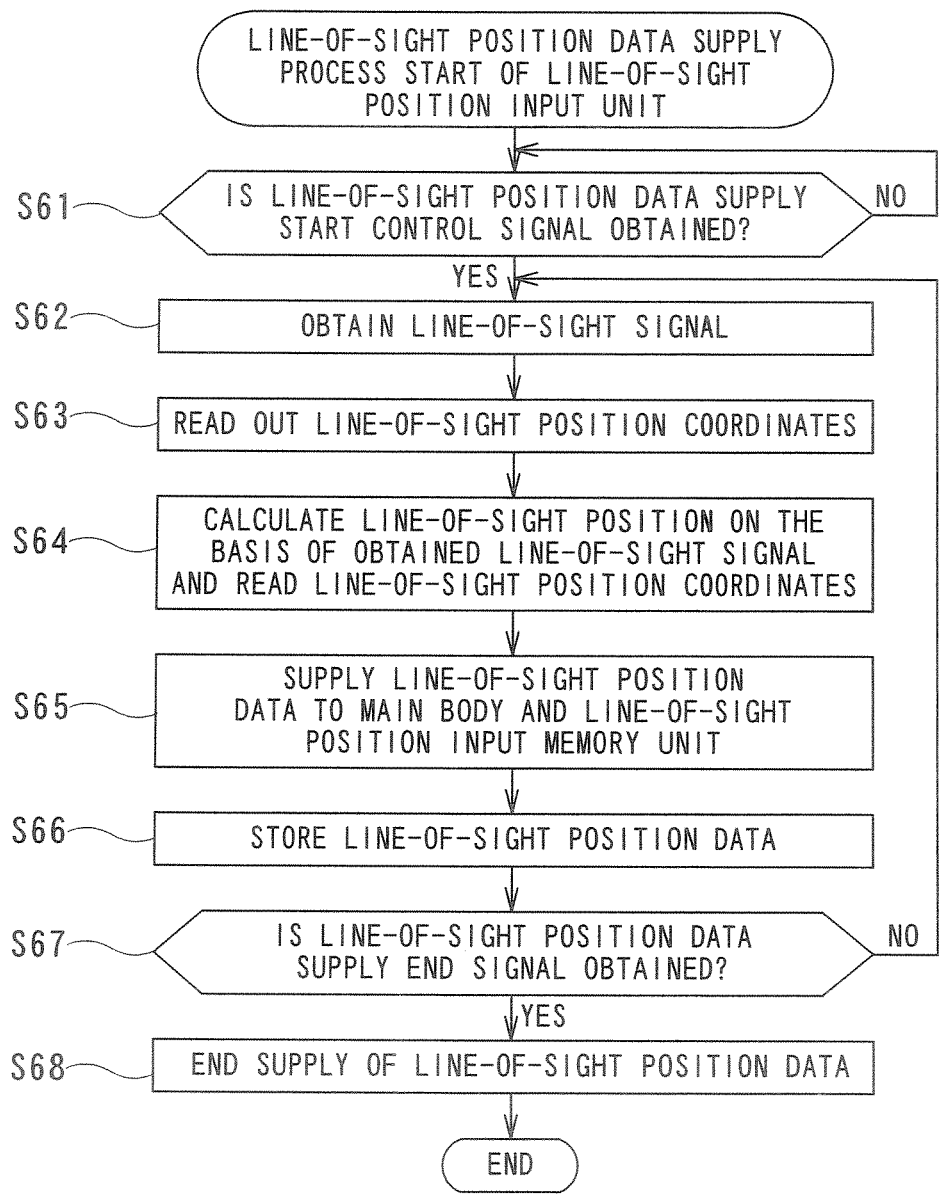
FIG. 10 is a flowchart for describing line-of-sight position data supply processing of the line-of-sight position input unit in FIG. 1.

Also, the line-of-sight position input control unit 41 obtains the line-of-sight position data supply start control signal supplied from the control unit 21 of the main body 11, and starts a line-of-sight position data supply process to the main body 11 (as will be described later while referring to the flowchart of FIG. 10) on the basis of thus obtained line-of-sight position data supply start control signal The line-of-sight position input control unit 41 obtains the line-of-sight position data end control signal supplied from the control unit 21 of the main body 11 and on the basis of the thus obtained line-of-sight position data end control signal, ends the line-of-sight position data supply process to the main body 11.

That is, after the line-of-sight position data supply start control signal is obtained from the control unit 21 of the main body 11 until a line-of-sight position data supply end control signal is obtained from the control unit 21 of the main body 11, the line-of-sight position input control unit 41 performs the supply of the line-of-sight position data to the main body 11 all the time.

Furthermore, the line-of-sight position input control unit 41 reads out line-of-sight position coordinates for calculating the line-of-sight position of the operator (hereinafter referred to as "line-of-sight position coordinates") from the line-of-sight position input memory unit 42 on the basis of the line-of-sight signal supplied from the eye ball camera 44 (that is, this corresponds to image data on the eye ball of the operator captured by the eye ball camera 44 and hereinafter, the same term usage applies), and calculates the current line-of-sight position of the operator on the basis of the read line-of-sight position coordinates and the thus obtained line-of-sight signal, whereby the line-of-sight position data that is data on the current line-of-sight position of the operator is supplied to the main body 11 and the line-of-sight position input memory unit 42.

The line-of-sight position input memory unit 42 previously stores the line-of-sight position coordinates for calculating the line-of-sight position of the operator on the basis of the line-of-sight signal supplied from the eye ball camera 44, and in accordance with the control of the line-of-sight position input control unit 41, appropriately supplies the line-of-sight position coordinates to the line-of-sight position input control unit 41. Also, the line-of-sight position input memory unit 42 stores the line-of-sight position data that is supplied from the line-of-sight position input control unit 41 and stores the thus obtained the line-of-sight position data therein.

The camera 43 is composed, for example, of an image pickup element such as a CCD (Charge Coupled Device) or a CMOS (Complementary Metal-Oxide Semiconductor). When the operator mounts the line-of-sight position input unit 14 to its head area, the line-of-sight position input unit 14 has been previously located at a predetermined position so that the screen of the display unit 15 can be captured. In accordance with the control of the line-of-sight position input control unit 41, appropriately, screen image data that is image data on the screen of the display unit 15 of the main body 11 captured by the camera 43 (hereinafter referred to as "screen image data") is supplied to the line-of-sight position input control unit 41.

The eye ball camera 44 is formed of, for example, an image pickup element such as a CCD (Charge Coupled Device) or a CMOS (Complementary Metal-Oxide Semiconductor). When the operator mounts the line-of-sight position input unit 14 to its head area, the line-of-sight position input unit 14 has been previously provided at a predetermined position so that the image of the eye balls of the operator can be captured. Appropriately, the line-of-sight signal that is image data of the eye balls of the operator captured by the eye ball camera 44 is supplied to the line-of-sight input control unit 41.

Figure 3:
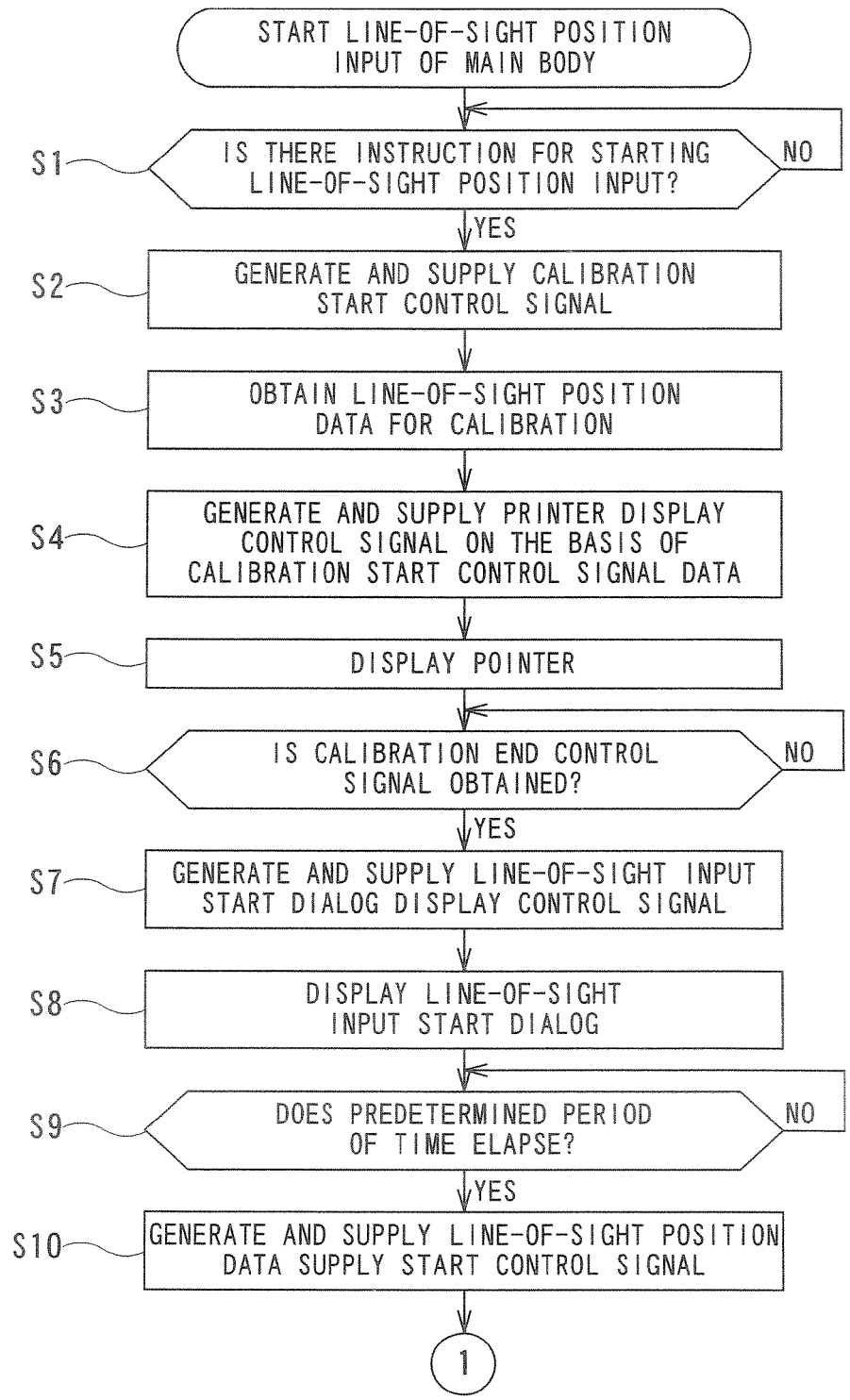
FIG. 3 is a flowchart for describing line-of-sight input processing of a main body.

With reference to flowcharts in FIGS. 3 and 4, a line-of-sight input process of the main body 11 of the ultrasonic diagnostic apparatus 1 in FIG. 1 will be described. It should be noted that this line-of-sight input process is started when the line-of-sight position input unit 14 is mounted to the head area of the operator after the B mode image is displayed on the display unit 15.

In Step S1, as the operator operates a keyboard (not shown) or a mouse (not shown) of the input unit (input means) 13, the control unit 21 determines whether or not there is an instruction for starting a line-of-sight input process and stands by until it is determined that there is an instruction for starting the line-of-sight input process.

In Step S1, if it is determined that there is an instruction for starting the line-of-sight input process, the control unit 21 generates in Step S2 the calibration start control signal that is a control signal for causing the line-of-sight position input unit 14 to start the calibration process to be supplied to the line-of-sight position input unit 14.

Now, with reference to the flowchart of FIG. 5, the calibration process of the line-of-sight position input unit 14 of the ultrasonic diagnostic apparatus 1 in FIG. 1 corresponding to the calibration start control signal supply process in Step S2 of FIG. 3 will be described.

In Step S41, the line-of-sight position input control unit 41 determines whether or not the calibration start control signal supplied from the control unit 21 of the main body 11 is obtained and stands by until it is determined that the calibration start control signal is obtained.

In Step S41, if it is determined that the calibration start control signal is obtained, the line-of-sight position input control unit 41 obtains, in Step S42, the line-of-sight signal that is image data on the eye balls of the operator captured by the eye ball camera 44 from the eye ball camera 44.

In Step S43, the line-of-sight position input control unit 41 reads out the line-of-sight position coordinates previously stored in the line-of-sight position input memory unit 42. In Step S44, the line-of-sight position input control unit 41 calculates the current line-of-sight position of the operator on the basis of the thus obtained line-of-sight signal and the read out line-of-sight position coordinates.

Figure 6:
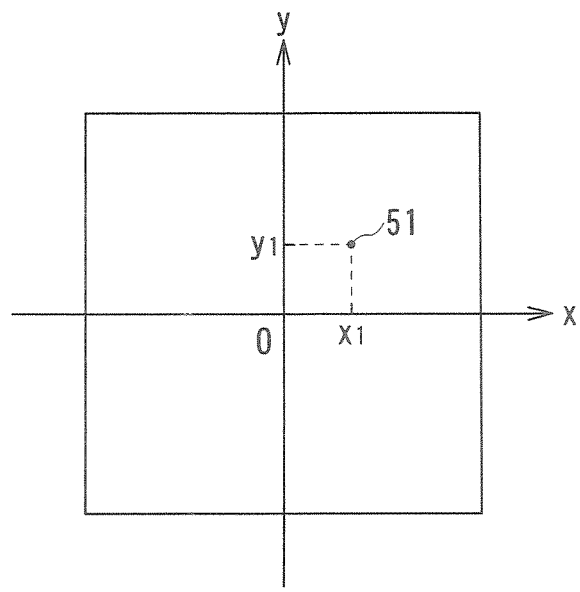
FIG. 6 is a diagram for describing a calculation method for a current line-of-sight position of the operator in the line-of-sight position input unit in FIG. 1.

With reference to FIG. 6, a calculation method of calculating the current line-of-sight position of the operator will be described.

As shown in FIG. 6, a point 51 represents the current line-of-sight position of the operator in the line-of-sight signal that is the image data of the eye balls of the operator captured by the eye ball camera 44. A horizontal axis represents an x axis of the line-of-sight position coordinates and a vertical axis represents a y axis of the line-of-sight position coordinates. In the case of FIG. 6, the current line-of-sight position of the operator is calculated to have the value of the x axis of x1 and the value of the y axis of y1 on the basis of the line-of-sight position coordinates (the x axis and the y axis). At this time, the current line-of-sight position of the operator is denoted by (x1, y1).

In Step S45, the line-of-sight position input control unit 41 supplies line-of-sight position data for calibration that is data on the calculated current line-of-sight position of the operator ("line-of-sight position data for calibration") to the main body 11. The line-of-sight position input control unit 41 supplies the calculated line-of-sight position data for calibration to the line-of-sight position input memory unit 42. In Step S46, the line-of-sight position input memory unit 42 obtains the line-of-sight position data for calibration supplied from the line-of-sight position input control unit 41 and stores the thus obtained line-of-sight position data for calibration.

Now, with reference to FIG. 3 again, a pointer display process of the main body 11 (processes in Step S3 to S5 in FIG. 3) to be performed while corresponding to the line-of-sight position data supply process for calibration in Step S45 of FIG. 5 in the line-of-sight position input unit 14 will be described.

Figure 7:
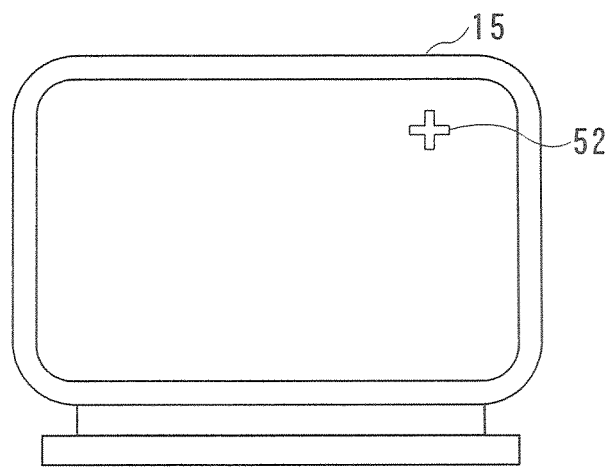
FIG. 7 shows a display example of a pointer displayed on a display unit in FIG. 1.

In Step S3, the line-of-sight position data obtaining unit 27 obtains the line-of-sight position data for calibration supplied from the line-of-sight position input unit 14 and also supplies the thus obtained line-of-sight position data for calibration to the control unit 21. In Step S4, the control unit 21 generates a point display control signal for displaying a pointer on the display unit 15 on the basis of the thus obtained line-of-sight position data for calibration to be supplied to the display unit 15. In Step S5, on the basis of the pointer display control signal supplied from the control unit 21, as shown in FIG. 7, the display unit 15 displays a pointer 52.

With reference back to FIG. 5, in Step S47, the line-of-sight position input control unit 41 obtains the screen image data captured by the camera 43 from the camera 43. That is, the screen image data captured by the camera 43 shown in FIG. 7 is obtained from the camera 43. In Step S48, on the basis of the thus obtained screen image data, the line-of-sight position input control unit 41 generates image position coordinates for calculating a position of the pointer on the display unit 15 of the main body 11. In Step S49, the line-of-sight position input control unit 41 calculates, on the basis of the generated image position coordinates, the display position of the pointer 52 displayed on the display unit 15 of the main body 11.

Figure 8:
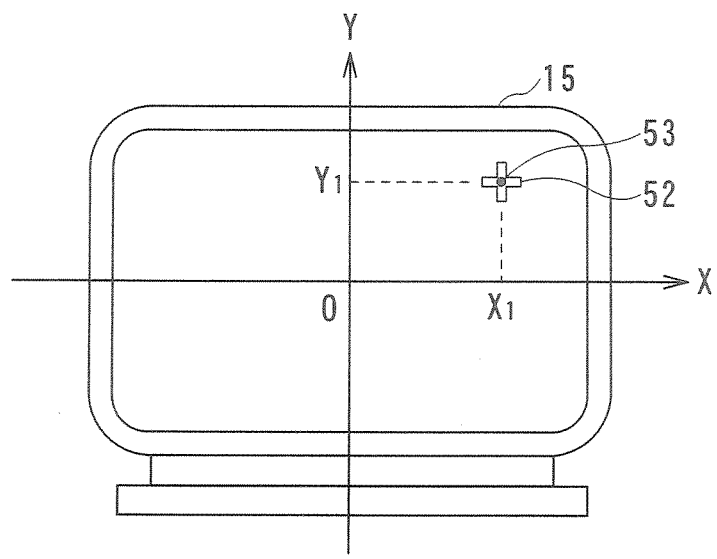
FIG. 8 is a diagram for describing a calculation method for a position of the pointer displayed on the display unit of the main body of the line-of-sight position input unit in FIG. 1.

With reference to FIG. 8, a calculation method of calculating the position of the pointer 52 to be displayed on the display unit 15 of the main body 11 will be described.

As shown in FIG. 8, a point 53 represents the center position of the pointer 52 to be displayed on the display unit 15 of the main body 11. A horizontal axis represents an X axis of the line-of-sight position coordinates and a vertical axis represents a Y axis of the line-of-sight position coordinates. In the case of FIG. 8, the center position of the pointer 52 is calculated as the current line-of-sight position of the operator, and the current line-of-sight position of the operator is calculated to the value of the X axis of X1 and the value of the Y axis of Y1 on the basis of the line-of-sight position coordinates (the X axis and the Y axis), for example. At this time, the position of the pointer 52 to be displayed on the display unit 15 of the main body 11 is denoted by (X1, Y1).

The line-of-sight position input control unit 41 supplies pointer display position data that is data on the calculated display position of the pointer 52 to the line-of-sight position input memory unit 42.

In Step S50, the line-of-sight position input memory unit 42 obtains the pointer display position data supplied from the line-of-sight position input control unit 41 and stores the thus obtained pointer display position data therein.

In Step S51, the line-of-sight position input control unit 41 reads out the line-of-sight position data for calibration and the pointer display position data stored in the line-of-sight position input memory unit 42. In Step S52, the line-of-sight position input control unit 41 determines on the basis of the read line-of-sight position data for calibration and the pointer display position data whether or not the line-of-sight position for calibration and the display position of the pointer 52 are matched to each other. That is, in the cases of FIGS. 6 and 7, it is judged whether or not the line-of-sight position for calibration (x1, y1) and the display position of the pointer 52 (X1, Y1) are matched to each other are matched to each other.

In Step S52, if it is determined that the line-of-sight position for calibration and the display position of the pointer are not are matched to each other, the line-of-sight position input control unit 41 adjusts the line-of-sight position coordinates in Step S53 so that the line-of-sight position for calibration and the display position of the pointer 52 are matched to each other. To be specific, in order that the line-of-sight position for calibration and the display position of the pointer 52 are matched to each other, the line-of-sight position coordinates (the x axis and the y axis) are shifted in parallel by predetermined values. The line-of-sight position input control unit 41 supplies the adjusted line-of-sight position coordinates to the line-of-sight position input memory unit 42.

In Step S54, the line-of-sight position input memory unit 42 stores the adjusted line-of-sight position coordinates supplied from the line-of-sight position input control unit 41.

In Step S52, if it is determined that the line-of-sight position for calibration and the display position of the pointer are matched to each other, the processes in Steps S53 and S54 are skipped. That is, in this case, the adjustment process on the line-of-sight position coordinates is not performed.

In Step S55, the line-of-sight position input control unit 41 generates a calibration end control signal and supplies the generated calibration end control signal to the main body 11.

In this way, as the calibration process is performed in the line-of-sight position input unit 14, in the case where the line-of-sight position data of the operator is supplied, the line-of-sight position input unit 14 can supply the current data on the correct line-of-sight position of the operator to the main body 11.

With reference to FIG. 3 again, in Step S6, the control unit 21 determines whether or not the calibration end control signal is obtained from the line-of-sight position input unit 14, and stands by until it is determined that the calibration end control signal is obtained.

In Step S6, if it is determined that the calibration end control signal is obtained, the control unit 21 generates in Step S7 a line-of-sight input start dialog display control signal for displaying a dialog for informing the start of the line-of-sight input, and supplies the generated line-of-sight input start dialog display control signal to the display unit 15. In Step S8, the display unit 15 displays the line-of-sight input start dialog 54 shown in FIG. 9 on the basis of the line-of-sight input start dialog display control signal supplied from the control unit 21.

Figure 9:
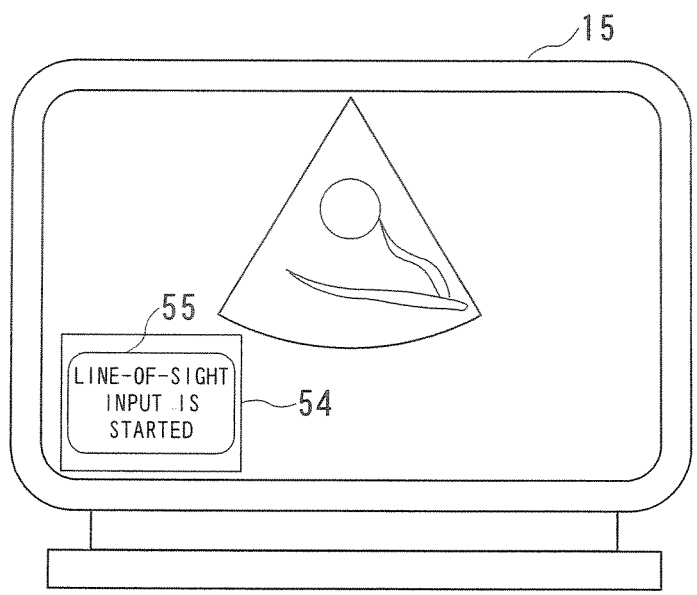
FIG. 9 shows a display example of a line-of-sight input start dialog displayed on the display unit in FIG. 1.

The line-of-sight input start dialog 54 in FIG. 9 has a message display column 55.

In the case of the example of FIG. 9, a message "line-of-sight input is stated" is displayed on the message display column 55. As a result, the operator understands that after this moment the line-of-sight input with use of the line-of-sight position input unit 14 can be conducted.

In Step S9, the control unit 21 determines whether or not a predetermined period of time previously set elapses on the basis of an incorporated timer that is not shown in the drawing, and stands by until it is determined that the predetermined period of time elapses. That is, until the previously set predetermined period of time elapses, the line-of-sight input start dialog 54 for informing the start of the line-of-sight input is displayed. As a result, until the previously set predetermined period of time elapses, the operator can check whether or not the line-of-sight input with use of the line-of-sight position input unit 14 can be conducted.

In Step S9, if it is determined that the predetermined time elapses, the control unit 21 in Step S10 generates the line-of-sight position data supply start control signal for causing the line-of-sight position input unit 14 to start the supply of the current line-of-sight position data of the operator, and supplies the generated line-of-sight position data supply start control signal to the line-of-sight position input unit 14.

Next, with reference to the flowchart of FIG. 10, the line-of-sight position data supply process of the line-of-sight position input unit 14 of the ultrasonic diagnostic apparatus 1 in FIG. 1 corresponding to the process in Step S10 in FIG. 3 will be described.

In Step S61, the line-of-sight position input control unit 41 determines whether or not the line-of-sight position data supply start control signal supplied from the control unit 21 of the main body 11 is obtained, and stands by until the line-of-sight position data supply start control signal supplied from the control unit 21 of the main body 11 is obtained.

In Step S61, if it is determined that the line-of-sight position data supply start control signal supplied from the control unit 21 of the main body 11 is obtained, the line-of-sight position input control unit 41 obtains in Step S62 the line-of-sight signal that is the image data of the eye balls of the operator captured by the eye ball camera 44 from the eye ball camera 44.

In Step S63, the line-of-sight position input control unit 41 reads out the line-of-sight position coordinates after the adjustment that is stored in the line-of-sight position input memory unit 42. In Step S64, the line-of-sight position input control unit 41 calculates the current line-of-sight position of the operator on the basis of the thus obtained line-of-sight signal and the read line-of-sight position coordinates after the adjustment.

In Step S65, the line-of-sight position input control unit 41 supplies the line-of-sight position data that is data on the current line-of-sight position of the operator to the main body 11 and the line-of-sight position input memory unit 42.

In Step S66, the line-of-sight position input memory unit 42 obtains the current line-of-sight position data of the operator supplied from the line-of-sight position input control unit 41 to store the thus obtained current line-of-sight position data of the operator.

In Step S67, the line-of-sight position input control unit 41 determines from the control unit 21 of the main body 11 whether or not the line-of-sight position data supply end control signal for ending the supply of the line-of-sight position data is obtained (through a process in Step S33 to be described later with reference to the control signal supplied from the main body 11 with reference to the flowchart in FIG. 4). In Step S67, if it is determined that from the control unit 21 of the main body 11, the line-of-sight position data supply end control signal for ending the supply of the line-of-sight position data is not obtained, the process precedes to Step S62, and the processes in Step S62 and thereafter are repeated. That is, until it is determined that the line-of-sight position data supply end control signal is obtained from the control unit 21 of the main body 11, the line-of-sight position input unit 14 keeps supplying the current line-of-sight position data of the operator to the main body 11.

As a result, until the line-of-sight position data supply end control signal is supplied to the line-of-sight position input unit 14, the main body 11 can keep obtaining the current line-of-sight position data of the operator and can display the pointer 52 on the basis of the thus obtained current line-of-sight position data of the operator.

In Step S67, if it is determined that the line-of-sight position data supply end control signal for ending the supply of the line-of-sight position data is obtained from the control unit 21 of the main body 11, the line-of-sight position input control unit 41 stops in Step S68 the supply of the current line-of-sight position data of the operator to the main body 11.

With reference to FIG. 4 again, in Step S11, the line-of-sight position data obtaining unit 27 obtains the current line-of-sight position data of the operator from the line-of-sight position input unit 14 and also supplies the thus obtained current line-of-sight position data of the operator to the control unit 21. In Step S12, on the basis of the line-of-sight position data (that is, the current line-of-sight position data of the operator) supplied from the line-of-sight position data obtaining unit 27, the control unit 21 generates a pointer display control signal for displaying the pointer 52 on the display unit 15 and supplies the generated pointer display control signal to the display unit 15.

In Step S13, the display unit 15 displays the pointer 52 on the basis of the pointer display control signal supplied from the control unit 21. As a result, the operator can find out where its own line-of-sight position exists on the screen of the display unit 15.

Figure 11:
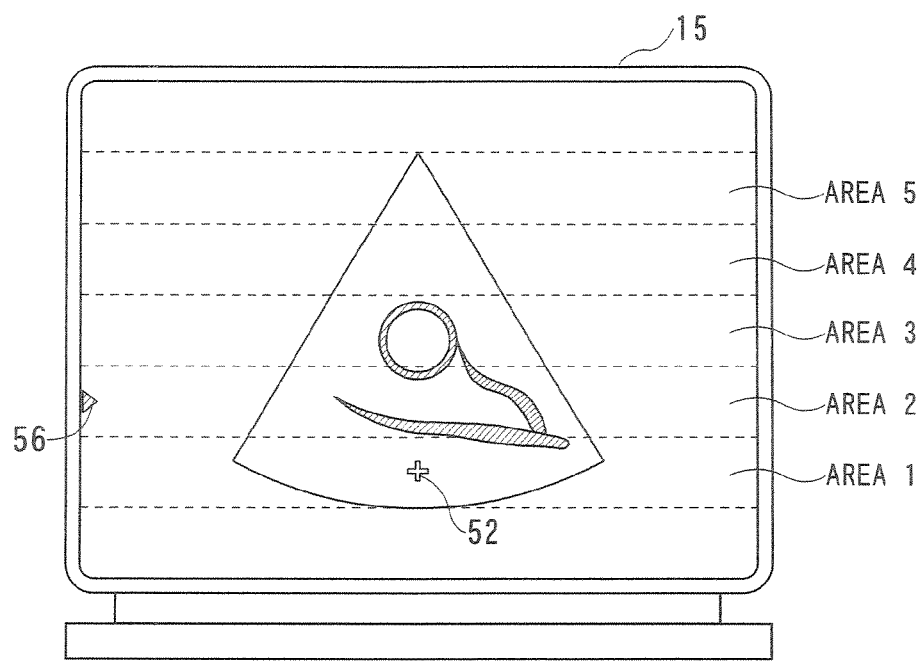
FIG. 11 shows a display example to be displayed on the display unit of FIG. 1.

FIG. 11 shows a display example of the pointer 52 on the display unit 15 together with the B mode image.

Herein, the screen to be displayed on the display unit 15 is previously divided into 5 areas from an area 1 to an area 5 in accordance with the focal point position of the ultrasonic beam at the time of the transmission, for example. As shown in FIG. 11, the pointer 52 is displayed on a predetermined position in the area 1 to be displayed on the display unit 15. This means that the current line-of-sight position of the operator is at the predetermined position of the area 1 to be displayed on the display unit 15.

Then, a triangular shaded area shown in FIG. 11 ("focal point position pointer 56") represents a current focal point position of the ultrasonic beam at the time of the transmission. In the case of FIG. 11, the current focal point position of the ultrasonic beam at the time of the transmission is set to be at a predetermined potion in the area 2 on the screen to be displayed on the display unit 15. It should be noted that before the start of the line-of-sight input process of the main body 11, the first focal point position of the ultrasonic beam at the time of the transmission is previously set to be at a predetermined potion in the area 2 on the screen to be displayed on the display unit 15. It is needless to say that the first focal point position of the ultrasonic beam at the time of the transmission may be previously set to be at another area on the screen to be displayed on the display unit 15.

In Step S14, the control unit 21 determines, on the basis of the line-of-sight position data supplied from the line-of-sight position data obtaining unit 27, whether or not the current line-of-sight position of the operator is out of the screen of the display unit 15. In Step S14, if it is determined that the current line-of-sight position of the operator is out of the screen of the display unit 15, the control unit 21 executes in Step S15 an error process, and then the process proceeds to Step S11 and the processes in Step S11 and thereafter are repeatedly performed.

In Step S14, if it is determined that the current line-of-sight position of the operator is not out of the screen of the display unit 15, the control unit 21 determines whether or not on the basis of the line-of-sight position data obtained in Step S16, the current line-of-sight position of the operator is out of the previously set predetermined area including the focal point position of the ultrasonic beam at the time of the transmission.

In the case of FIG. 11, the current line-of-sight position of the operator is at the predetermined position in the area 1 on the screen to be displayed on the display unit 15, and the area 2 is previously set as the predetermined area including the focal point position of the ultrasonic beam at the time of the transmission. It is thus determined that the current line-of-sight position of the operator is out of the predetermined area including the previously set focal point position of the ultrasonic beam at the time of the transmission.

In Step S16, if it is determined that the current line-of-sight position of the operator is not out of the predetermined area including the previously set focal point position of the ultrasonic beam at the time of the transmission (that is, if it is determined that the current line-of-sight position of the operator is within the previously set focal point position of the ultrasonic beam at the time of the transmission), the process proceeds to Step S11, and the processes in Step S11 and thereafter will be repeatedly performed.

In Step S16, if it is determined that the current line-of-sight position of the operator is out of the previously set focal point position of the ultrasonic beam at the time of the transmission, the control unit 21 determines on the basis of the line-of-sight position data obtained in Step S17, whether or not the current line-of-sight position of the operator stays in the same area over a predetermined period of time.

In Step S17, if it is determined that the current line-of-sight position of the operator stays in the same area over the predetermined period of time, the control unit 21 generates in Step S18 an area change control signal for changing an area to which the line-of-sight position of the operator belongs, and supplies the generated area change control signal to the setting condition change unit 26. The setting condition change unit 26 changes the predetermined area including the previously set focal point position of the ultrasonic beam at the time of the transmission to the area to which the current line-of-sight position of the operator belongs which is determined to elapse over the predetermined period of time on the basis of the area change control signal supplied from the control unit 21, and supplies area data that is data on the changed area to a data memory unit 32.

Figure 12:
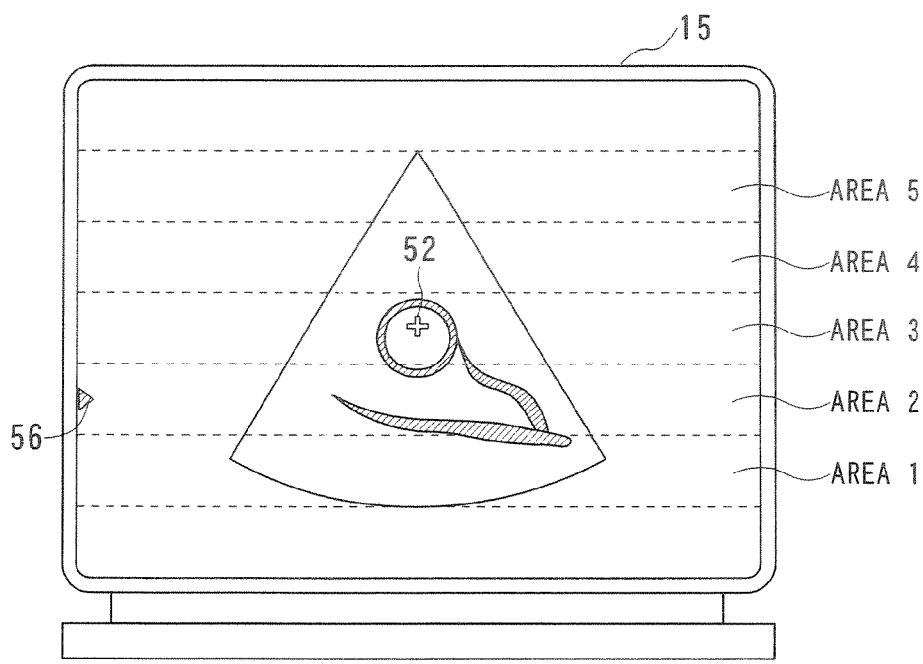
FIG. 12 shows a display example to be displayed on the display unit of FIG. 1.

In the case of FIG. 12, the area to which the current line-of-sight position of the operator belongs is in the area 3, and if a predetermined period of time elapses in the area, the predetermined area including the focal point position of the ultrasonic beam at the time of the transmission is changed from the area 2 to the area 3.

In this way, on the basis of the current line-of-sight position data of the operator supplied from the line-of-sight position input unit 14, the set predetermined area including the focal point position of the ultrasonic beam at the time of the transmission can be changed to an area desired by the operator.

It should be noted that if the previously set area is already changed to a new area through the line-of-sight input process of the main body 11 before the line-of-sight input process of the main body 11, the line-of-sight input process on the basis of the currently set area after the change. The same applies to changes in the focal point position and the image quality setting condition to be described later.

In Step S19, the data memory unit 32 obtains the area data supplied from the setting condition change unit 26 and stores the thus obtained area data therein. In Step S20, the control unit 21 reads out the area data stored in the data memory unit 32 and reads out a focal point position setting condition database managed by the focal point position setting condition database 33. Then, the read area data and the focal point position setting condition database are supplied to the setting condition change unit 26.

Figures 13, 14:
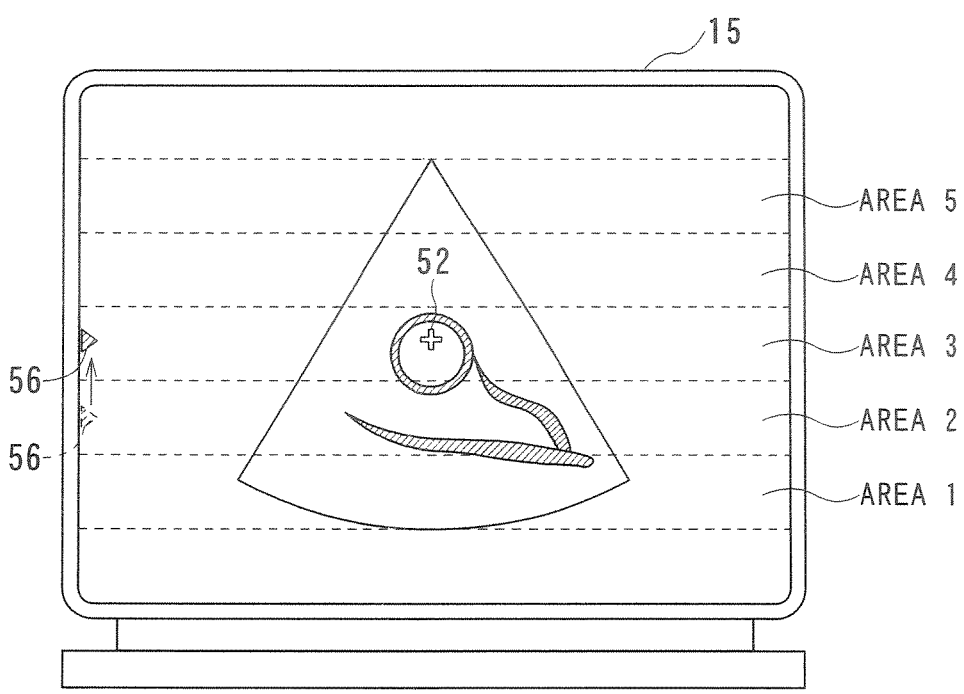
FIG. 13 shows an example of a focal point position setting condition database stored in a memory unit of the main body in FIG. 1.
FIG. 14 shows a display example to be displayed on the display unit of FIG. 1.

FIG. 13 shows an example of the focal point position setting condition database managed by the focal point position setting condition database 33.

"Area" and "focal point position" are described in association with each other in the first and second columns in the focal point position setting condition database 33 in FIG. 13, and respectively represent the area previously divided in accordance with the focal point position of the ultrasonic beam at the time of the transmission and the focal point position of the ultrasonic beam at the time of the transmission when the line-of-sight position of the operator is present in the corresponding area.

In the case of the first column in FIG. 13, it is shown that "area" is "area 1" and the area previously divided in accordance with the focal point position of the ultrasonic beam at the time of the transmission is "area 1". In addition, it is shown that "focal point position" is "D1" and when the focal point position of the ultrasonic beam at the time of the transmission when the line-of-sight position of the operator is present in the corresponding are is "D1".

It should be noted that the focal point position of the ultrasonic beam at the time of the transmission is previously set to a representative value of the focal point position in a range included in the corresponding area, for example, an intermediate value of the focal point position in a range included in the corresponding area. Of course, as long as the focal point position is in a range included in the corresponding area, any focal point position may be used. Hereinafter, the same applies to the second to fifth columns in FIG. 13.

In the case of the second column in FIG. 13, it is shown that "area" is "area 2" and the area previously divided in accordance with the focal point position of the ultrasonic beam at the time of the transmission is "area 2". In addition, it is shown that "focal point position" is "D2" and when the focal point position of the ultrasonic beam at the time of the transmission when the line-of-sight position of the operator is present in the corresponding are is "D2".

In the case of the third column in FIG. 13, it is shown that "area" is "area 3" and the area previously divided in accordance with the focal point position of the ultrasonic beam at the time of the transmission is "area 3". In addition, it is shown that "focal point position" is "D3" and when the focal point position of the ultrasonic beam at the time of the transmission when the line-of-sight position of the operator is present in the corresponding are is "D3".

In the case of the fourth column in FIG. 13, it is shown that "area" is "area 4" and the area previously divided in accordance with the focal point position of the ultrasonic beam at the time of the transmission is "area 4". In addition, it is shown that "focal point position" is "D4" and when the focal point position of the ultrasonic beam at the time of the transmission when the line-of-sight position of the operator is present in the corresponding are is "D4".

In the case of the fifth column in FIG. 13, it is shown that "area" is "area 5" and the area previously divided in accordance with the focal point position of the ultrasonic beam at the time of the transmission is "area 5". In addition, it is shown that "focal point position" is "D5" and when the focal point position of the ultrasonic beam at the time of the transmission when the line-of-sight position of the operator is present in the corresponding are is "D5".

In Step S21, the setting condition change unit 26 changes the currently set focal point position with reference to the focal point position setting condition database supplied via the control unit 21 from the focal point position setting condition database 33 on the basis of the area data supplied via the control unit 21 from the data memory unit 32. The setting condition change unit 26 supplies the focal point position data that is data on the changed focal point position to the data memory unit 32.

In the example of FIG. 12, the area including the current line-of-sight position of the operator is the area 3, and thus the focal point position of the ultrasonic beam at the time of the transmission is changed from "D2" to "D3".

In Step S22, the data memory unit 32 obtains the focal point position data supplied from the setting condition change unit 26 and stores the thus obtained focal point position data therein. In Step S23, the control unit 21 reads out the focal point position data stored in the data memory unit 32.

In Step S24, the control unit 21 generates a focal point position shift control signal for shifting the focal point position to the changed predetermined focal point position on the basis of the read focal point position data and supplies the generated focal point position shift control signal to the transmission unit 22 and the reception signal supplied from the reception unit 23. In Step S25, on the basis of the focal point position shift control signal supplied from the control unit 21, the transmission unit 22 gives a delay time to the rate pulse so that the focal point position is shifted to the changed predetermined focal point position to be supplied to a pulsar not shown in the drawing of the transmission unit 22. Also, on the basis of the focal point position shift control signal supplied from the control unit 21, the reception delay circuit gives such a delay time that the delay time given by the transmission delay circuit of the transmission unit 22 is set to be returned to the echo signal supplied from the preamplifier after the amplification to be then supplied to the adder circuit.

In the case of FIG. 12, when the set focal point position is "D2" and a predetermined period of time elapses after the line-of-sight position of the operator is the area 3, as shown in FIG. 14, the focal point position pointer 56 is shifted in a direction of an arrow of FIG. 14. That is, the focal point position of the ultrasonic beam at the time of the transmission is shifted from "D2" to "D3". In this way, on the basis of the current line-of-sight position data of the operator supplied from the line-of-sight position input unit 14, the set focal point position can be changed and shifted to a focal point position desired by the operator.

Herein, as the ultrasonic beam converges in the vicinity of the focal point position of the ultrasonic beam at the time of the transmission, the diameter of the beam becomes smaller and the acoustic power level of the ultrasonic beam is increased. Thus, in the target area to be displayed on the display unit 15, it is possible to display a high quality image with higher spatial resolution as well as higher contrast.

Therefore, the ultrasonic diagnostic apparatus 1 according to the embodiment of the present invention changes and shifts the focal point position to the focal point position desired by the operator on the basis of the current line-of-sight position data of the operator supplied from the line-of-sight position input unit 14, and thus it is possible to display the high quality image with the high spatial resolution as well as the high contrast in the vicinity of the focal point position desired by the operator.

In Step S26, the control unit 21 generates a focal point position shift dialog display control signal for displaying a dialog for informing of the shift of the focal point position and supplies the generated focal point position shift dialog display control signal to the display unit 15. In Step S27, on the basis of the focal point position shift dialog display control signal supplied from the control unit 21, the display unit 15 displays the focal point position shift dialog 61 shown in FIG. 15.

Figure 15:
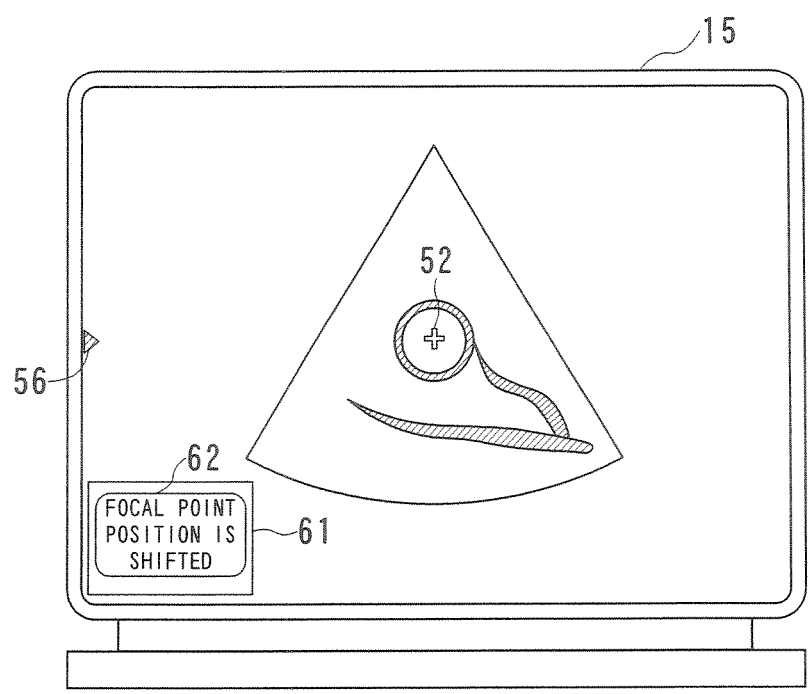
FIG. 15 shows a display example of a focal point position shift dialog to be displayed on the display unit of FIG. 1.

The focal point position shift dialog 61 in FIG. 15 has a message display column 62.

In an example of FIG. 15, the message display column 62 displays a message "focal point position is shifted". As a result, the operator can find out that the focal point position is shifted through the line-of-sight input process of the main body 11. It should be noted that when a predetermined period of time previously set elapses, the focal point position shift dialog 61 is not displayed. Also, according to the embodiment of the present invention, an example is shown in which a message based on texts is displayed, but a message based on a mark such as an icon or a character may also be used.

In Step S28, the control unit 21 reads out the area data stored in the data memory unit 32 and the image quality setting condition database managed by the image quality setting condition database 34 to be supplied to the setting condition change unit 26.

FIG. 16 shows an example of the image quality setting condition database managed by the image quality setting condition database 34.

"Area", "transmission waveform of ultrasonic wave", "transmission frequency", "transmission wave number", "reception frequency", and "acoustic power level of ultrasonic wave" are described in association to each other in the first to fifth columns in FIG. 16 and respectively represent the area previously divided in accordance with the focal point position of the ultrasonic beam at the time of the transmission, a type of a curve shape for representing a change over time in the ultrasonic wave transmitted from the ultrasonic probe 12, the number of repetition in unit time of the ultrasonic wave transmitted from the ultrasonic probe 12, the number of waves radiated by a wave determined by a transmission frequency, a frequency at the center of a frequency band used for visualization with respect to ultrasonic reception signal received while reflected from the living body, and a value in dB of an energy of the ultrasonic wave passing through a predetermined surface of the ultrasonic wave transmitted from the ultrasonic probe 12 in one second. It should be noted that "transmission waveform of ultrasonic wave", "transmission frequency", "transmission wave number", "reception frequency", and "acoustic power level of ultrasonic wave" in the second to fifth columns in FIG. 16 are registered in association with an optimal condition for each "area" in the first column in FIG. 16. That is, optimal conditions are registered with association in the predetermined focal point position previously set for each "area" in the first column in FIG. 16.

In the case of the first row in FIG. 16, it is shown that "area" is "area 1", and the area previously divided in accordance with the focal point position of the ultrasonic beam at the time of the transmission. It is also shown that "transmission waveform of ultrasonic wave" is "b1" and the type of the curve shape for representing a change over time in the ultrasonic wave transmitted from the ultrasonic probe 12 is "b1". In addition, it is shown that "transmission frequency" is "c1" and the frequency of the ultrasonic wave transmitted from the ultrasonic probe 12 is "c1". Then, it is shown that "transmission wave number" is "d1" and the number of waves radiated by the wave determined by a transmission frequency is "d1". Furthermore, it is shown that "reception frequency" is "e1" and the frequency at the center of a frequency band used for visualization with respect to ultrasonic reception signal received while reflected from the living body is "e1" Moreover, it is shown that "acoustic power level of ultrasonic wave" is "f1" and the value in dB of an energy of the ultrasonic wave passing through a predetermined surface of the ultrasonic wave transmitted from the ultrasonic probe 12 in one second is "f1".

In the case of the second row in FIG. 16, it is shown that "area" is "area 2", and the area previously divided in accordance with the focal point position of the ultrasonic beam at the time of the transmission. It is also shown that "transmission waveform of ultrasonic wave" is "b2" and the type of the curve shape for representing a change over time in the ultrasonic wave transmitted from the ultrasonic probe 12 is "b2". In addition, it is shown that "transmission frequency" is "c2" and the frequency of the ultrasonic wave transmitted from the ultrasonic probe 12 is "c2". Then, it is shown that "transmission wave number" is "d2" and the number of waves radiated by the wave determined by a transmission frequency is "d2". Furthermore, it is shown that "reception frequency" is "e2" and the frequency at the center of a frequency band used for visualization with respect to ultrasonic reception signal received while reflected from the living body is "e2". Moreover, it is shown that "acoustic power level of ultrasonic wave" is "f2" and the value in dB of an energy of the ultrasonic wave passing through a predetermined surface of the ultrasonic wave transmitted from the ultrasonic probe 12 in one second is "f2".

In the case of the third row in FIG. 16, it is shown that "area" is "area 3", and the area previously divided in accordance with the focal point position of the ultrasonic beam at the time of the transmission. It is also shown that "transmission waveform of ultrasonic wave" is "b3" and the type of the curve shape for representing a change over time in the ultrasonic wave transmitted from the ultrasonic probe 12 is "b3". In addition, it is shown that "transmission frequency" is "c3" and the frequency of the ultrasonic wave transmitted from the ultrasonic probe 12 is "c3". Then, it is shown that "transmission wave number" is "d3" and the number of waves radiated by the wave determined by a transmission frequency is "d3". Furthermore, it is shown that "reception frequency" is "e3" and the frequency at the center of a frequency band used for visualization with respect to ultrasonic reception signal received while reflected from the living body is "e3". Moreover, it is shown that "acoustic power level of ultrasonic wave" is "f3" and the value in dB of an energy of the ultrasonic wave passing through a predetermined surface of the ultrasonic wave transmitted from the ultrasonic probe 12 in one second is "f3".

In the case of the fourth row in FIG. 16, it is shown that "area" is "area 4", and the area previously divided in accordance with the focal point position of the ultrasonic beam at the time of the transmission. It is also shown that "transmission waveform of ultrasonic wave" is "b4" and the type of the curve shape for representing a change over time in the ultrasonic wave transmitted from the ultrasonic probe 12 is "b4". In addition, it is shown that "transmission frequency" is "c4" and the frequency of the ultrasonic wave transmitted from the ultrasonic probe 12 is "c4". Then, it is shown that "transmission wave number" is "d4" and the number of waves radiated by the wave determined by a transmission frequency is "d4". Furthermore, it is shown that "reception frequency" is "e4" and the frequency at the center of a frequency band used for visualization with respect to ultrasonic reception signal received while reflected from the living body is "e4". Moreover, it is shown that "acoustic power level of ultrasonic wave" is "f4" and the value in dB of an energy of the ultrasonic wave passing through a predetermined surface of the ultrasonic wave transmitted from the ultrasonic probe 12 in one second is "f4".

In the case of the fifth row in FIG. 16, it is shown that "area" is "area 5", and the area previously divided in accordance with the focal point position of the ultrasonic beam at the time of the transmission. It is also shown that "transmission waveform of ultrasonic wave" is "b5" and the type of the curve shape for representing a change over time in the ultrasonic wave transmitted from the ultrasonic probe 12 is "b5". In addition, it is shown that "transmission frequency" is "c5" and the frequency of the ultrasonic wave transmitted from the ultrasonic probe 12 is "c5". Then, it is shown that "transmission wave number" is "d5" and the number of waves radiated by the wave determined by a transmission frequency is "d5". Furthermore, it is shown that "reception frequency" is "e5" and the frequency at the center of a frequency band used for visualization with respect to ultrasonic reception signal received while reflected from the living body is "e5". Moreover, it is shown that "acoustic power level of ultrasonic wave" is "f5" and the value in dB of an energy of the ultrasonic wave passing through a predetermined surface of the ultrasonic wave transmitted from the ultrasonic probe 12 in one second is "f5".

In Step S29, with reference to the image quality setting condition database supplied via the control unit 21 from the image quality setting condition database 34, on the basis of the via area data the control unit 21 supplied from the data memory unit 32, the set image quality setting condition is changed.

In the case of FIG. 14, as "area" to which the current line-of-sight position of the operator belongs is "area 3", the image quality setting condition corresponding to the set focal point position is changed from the image quality setting condition corresponding to "area 2" (the image quality setting condition in which "transmission waveform of ultrasonic wave" is "b2", "transmission frequency" is "c2", "transmission wave number" is "d2", "reception frequency" is "e2", and "acoustic power level of ultrasonic wave" is "f2") to the image quality setting condition corresponding to "area 3" (the image quality setting condition in which "transmission waveform of ultrasonic wave" is "b3", "transmission frequency" is "c3", "transmission wave number" is "d2", "reception frequency" is "e3", and "acoustic power level of ultrasonic wave" is "f3").

The setting condition change unit 26 supplies image quality setting condition data that is data related to the changed image quality setting condition (the image quality setting condition in which "transmission waveform of ultrasonic wave" is "b3", "transmission frequency" is "c3", "transmission wave number" is "d2", "reception frequency" is "e3" and "acoustic power level of ultrasonic wave" is "f3") to the control unit 21. The control unit 21 generates an image quality setting condition change control signal on the basis of the image quality setting condition data supplied from the setting condition change unit 26 and supplies the generated image quality setting condition change control signal to the transmission unit 22 and the reception signal supplied from the reception unit 23. The transmission unit 22 and the reception signal supplied from the reception unit 23 respectively change the previously set image quality setting conditions to new image quality setting conditions on the basis of the image quality setting condition change control signal supplied from the control unit 21.

In this way, on the basis of the current line-of-sight position data of the operator, the operator can change and shift the focal point position to the desired position and also can change the image quality setting condition to the optimal image quality setting condition in the focal point position. As a result, while the operator only shifts its own line-of-sight, the focal point position can be automatically changed and shifted to the focal point position desired by the operator, the image quality setting condition can be automatically changed to the optimal image quality setting condition in the focal point position. Therefore, the operability of the ultrasonic diagnostic apparatus 1 can be improved.

In Step S30, the control unit 21 generates an image quality setting condition change dialog display control signal for displaying a dialog for informing of the change in the image quality setting condition and supplies the generated image quality setting condition change dialog display control signal to the display unit 15.

Figure 17:
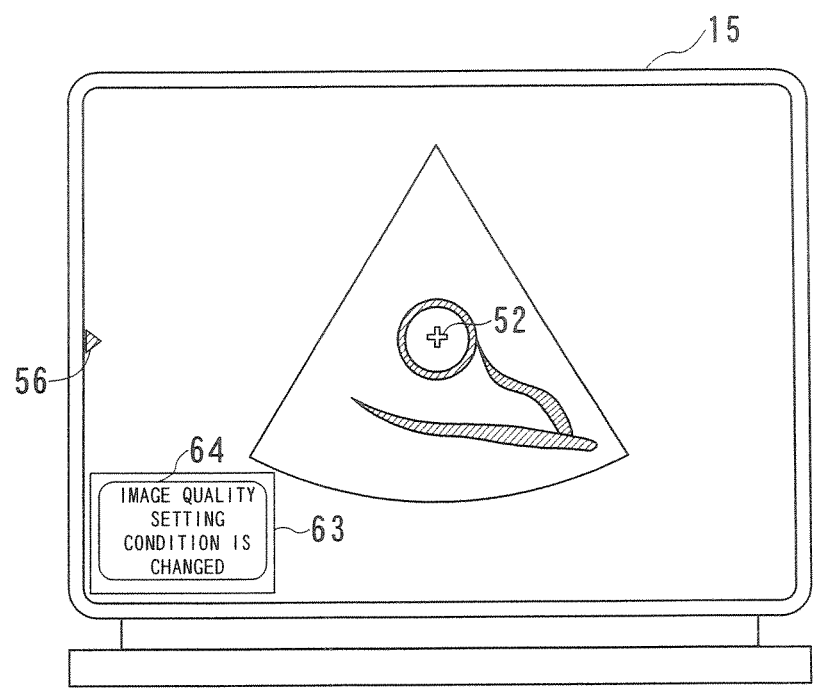
FIG. 17 shows a display example of to be displayed on the display unit of FIG. 1 an image quality setting condition change dialog.

In Step S31, the display unit 15 displays, on the basis of the image quality setting condition change dialog display control signal supplied from the control unit 21 the image quality setting condition change dialog 63 shown in FIG. 17.

The image quality setting condition change dialog 63 in FIG. 17 has a message display column 64.

In the example of FIG. 17, a message "image quality setting condition is changed" is displayed on the message display column 64. As a result, the operator can understand that the image quality setting condition is changed through the line-of-sight input process of the main body 11. It should be noted that the image quality setting condition change dialog 63 is not displayed when a previously set predetermined period of time elapses. Also, according to the embodiment of the present invention, an example is shown in which a message based on texts is displayed, but a message based on a mark such as an icon or a character may also be used.

In Step S32, the control unit 21 determines whether or not there is an instruction for ending the line-of-sight input process when the operator operates a key board (not shown) or a mouse (not shown) of the input unit 13.

In Step S32, if it is determined that there is no instruction for ending the line-of-sight input process, the process returns to Step S11 and the process in Step S11 is repeatedly performed. As a result, until the operator issues the instruction for ending the line-of-sight input process, the current line-of-sight position data of the operator is obtained any number of times. Then, on the basis of the thus obtained current line-of-sight position data of the operator, it is possible to change and shift the focal point position to the focal point position desired by the operator and change the image quality setting condition to the image quality setting condition that is optimal in the focal point position.

In Step S32, if it is determined that there is an instruction for ending the line-of-sight input process, the control unit 21 generates in Step S33 the line-of-sight position data supply end control signal for causing the line-of-sight position input unit 14 to end the supply of the line-of-sight position data and supplies the generated line-of-sight position data supply end control signal to the line-of-sight position input unit 14. After that, the line-of-sight input process of the main body 11 is ended.

On the other hand, in Step S17, if it is determined that the current line-of-sight position of the operator does not stay over the predetermined time, the process returns to Step S11 and the processes in Step S11 and thereafter will be repeatedly performed. To be specific, in the case where the line-of-sight position of the operator is shifted to the outside of the predetermined area previously set, such a process is performed when the line-of-sight position is shifted to the outside of the predetermined area previously set as the line-of-sight position is not present in the same area before the predetermined period of time elapses or the line-of-sight position is shifted to the previously set predetermined area as the line-of-sight position is not present in the same area before the predetermined period of time elapses.

As a result, for example, in the case where the focal point position is already shifted to the focal point position desired by the operator and also the image quality setting condition is changed to the image quality setting condition that is optimal in the focal point position, even when the operator shifts the line-of-sight to a non-desired area, if the operator shifts the line-of-sight from the non-desired area to the desired area within a previously set predetermined period of time, the operator can keep performing the operation with the current focal point position and the image quality setting condition. Therefore, the operability of the ultrasonic diagnostic apparatus can be improved.

According to the embodiment of the present invention, the current line-of-sight position data of the operator is sequentially obtained, and on the basis of the thus obtained current line-of-sight position data of the operator, it is possible that the focal point position is changed and shifted to the focal point position desired by the operator and also the image quality setting condition is changed to the image quality setting condition that is optimal in the focal point position. As a result, as the operator only shifts its own line-of-sight, the focal point position can be automatically shifted to the focal point position desired by the operator and also the image quality setting condition can be automatically changed to the image quality setting condition that is optimal in the focal point position.

As a result, in general, as compared with other medical diagnostic apparatuses such as an X-ray diagnostic apparatus and X-ray CT apparatus, with the ultrasonic diagnostic apparatus 1 in which the operator has a difficulty of adjusting the setting on the image quality, without depending on whether the operator performs a good or bad operation, the performance of the ultrasonic diagnostic apparatus 1 is exerted as much as possible, whereby it is possible that the image quality of the image displayed on the display unit 15 (for instance, the B mode image, the Doppler mode image, or the like) is improved.

In addition, in the case where the operator is a doctor, as the focal point position and the like can be operated only by shifting its own line-of-sight, the intermediation of another operator for performing a dedicated operation on the image quality setting condition of the ultrasonic diagnostic apparatus 1 (for example, a technician or the like). Even during the operation, while having a communication with a patient, the focal point position can be automatically changed and shifted to the focal point position desired by the operator and the image quality setting condition can be automatically changed to the image quality setting condition that is optimal in the focal point position, in a short period of time and in real time.

Therefore, the operability of the ultrasonic diagnostic apparatus 1 can be improved.

It should be noted that in the line-of-sight input process of the main body 11 described with reference to the flowcharts in FIGS. 3 and 4, on the basis of the thus obtained line-of-sight position data of the operator, after the focal point position of the ultrasonic beam at the time of the transmission is shifted, the previously set image quality setting condition is automatically changed to the image quality setting condition that is optimal in the shifted focal point position. For example, after the focal point position of the ultrasonic beam at the time of the transmission is shifted, the operator may choose whether or not the previously set image quality setting condition is changed to the image quality setting condition that is optimal in the shifted focal point position. The line-of-sight input process of the main body 11 in this case is shown in the flowcharts in FIGS. 18 and 19.

Figure 18:
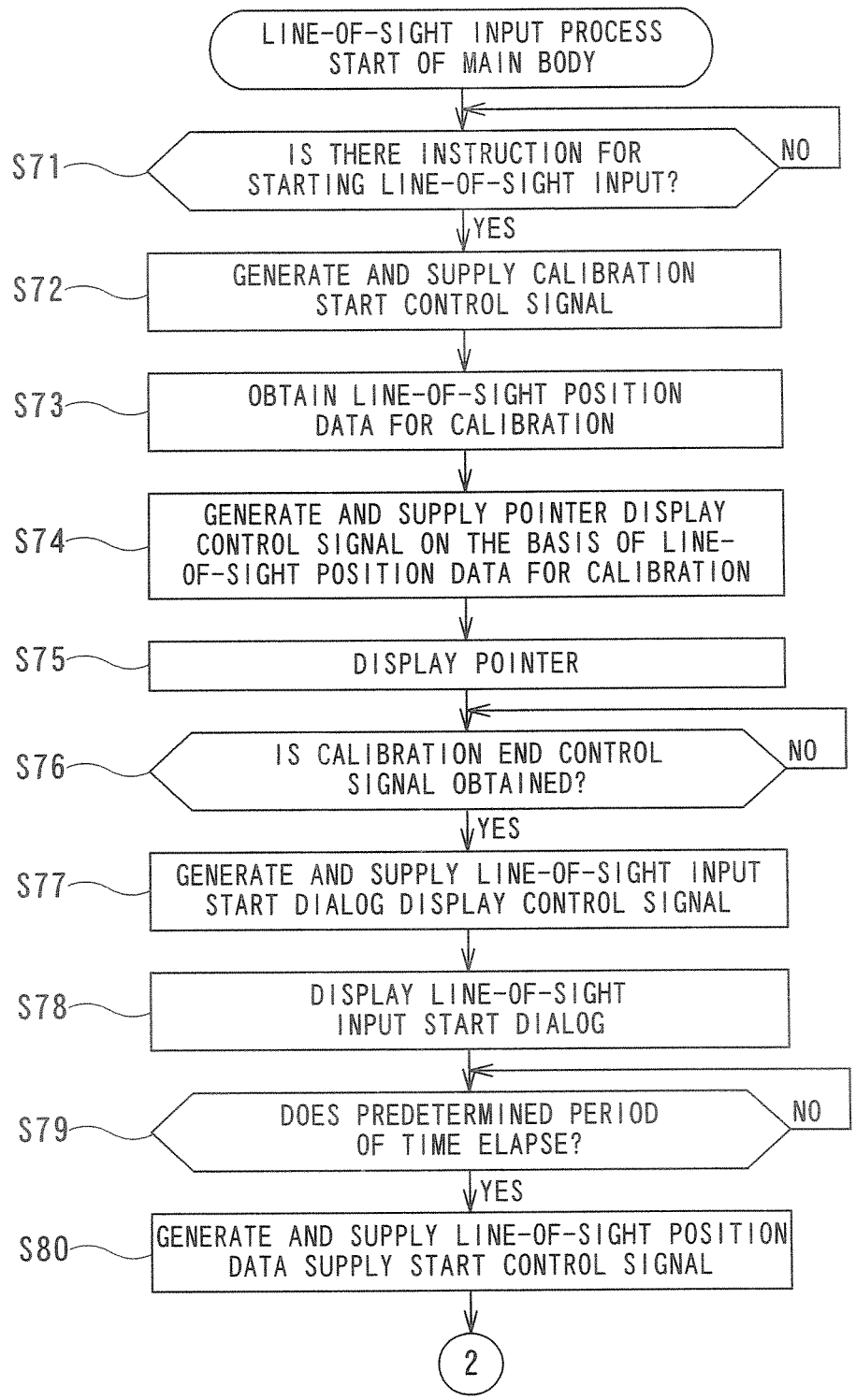
FIG. 18 is a flowchart for describing another line-of-sight input processing of the main body in FIG. 1.
Figure 19:
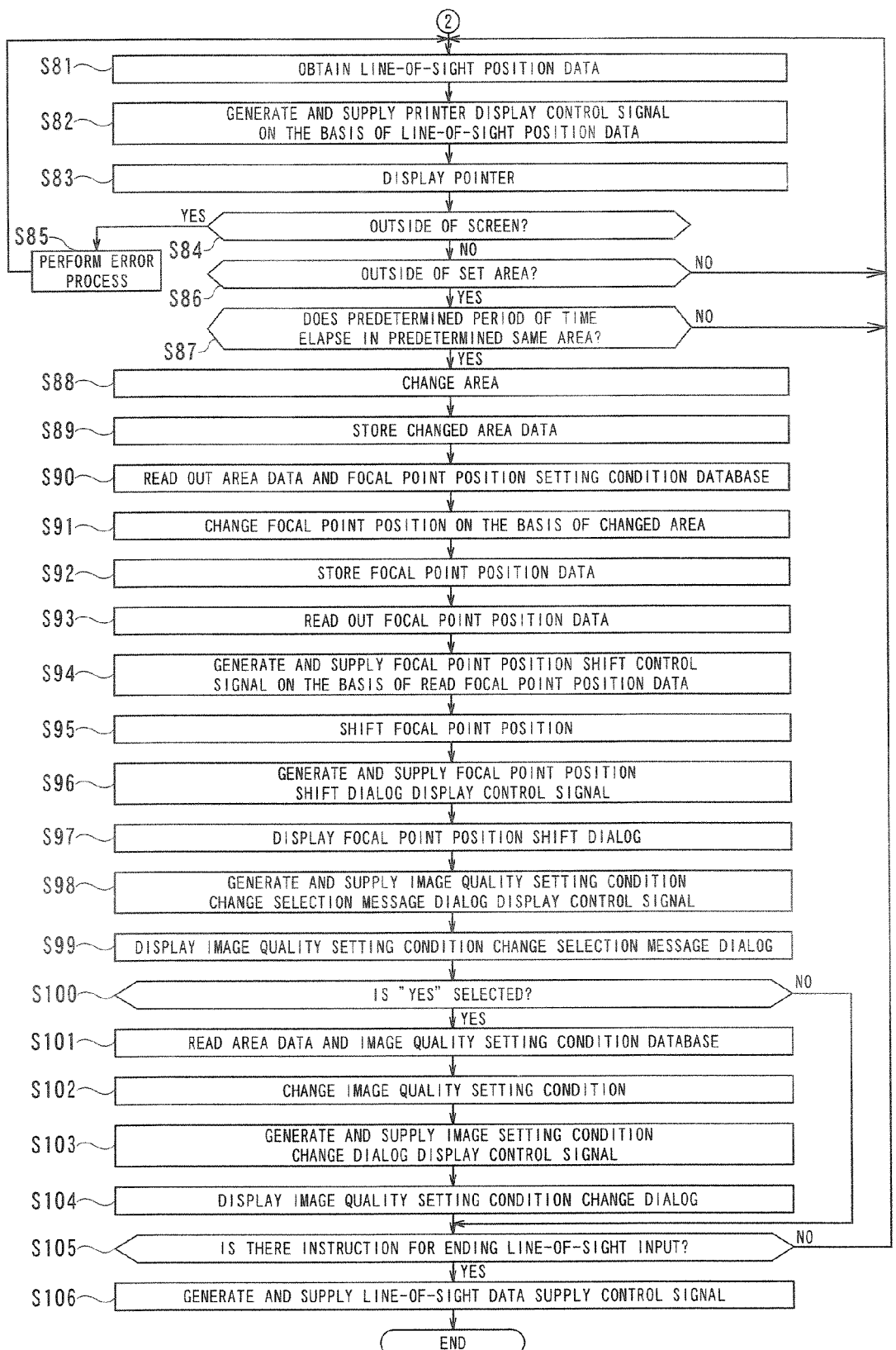
FIG. 19 is a flowchart for describing another line-of-sight input processing of the main body in FIG. 1.

With reference to the flowcharts in FIGS. 18 and 19, another line-of-sight input process of the main body 11 of the ultrasonic diagnostic apparatus 1 in FIG. 1 will be described. It should be noted that the processes in Steps S71 to S97 in FIGS. 18 and 19 and the processes in Steps S101 to S106 are similar to the processes in Steps S1 to S33 in FIGS. 3 and 4, the description will be omitted to avoid the repetition.

In Step S98, the control unit 21 generates an image quality setting condition change selection message dialog display control signal for displaying a message for causing the operator to choose whether or not the image quality setting condition change selection is changed, and supplies the generated image quality setting condition change selection message dialog display control signal to the display unit 15.

Figure 20:
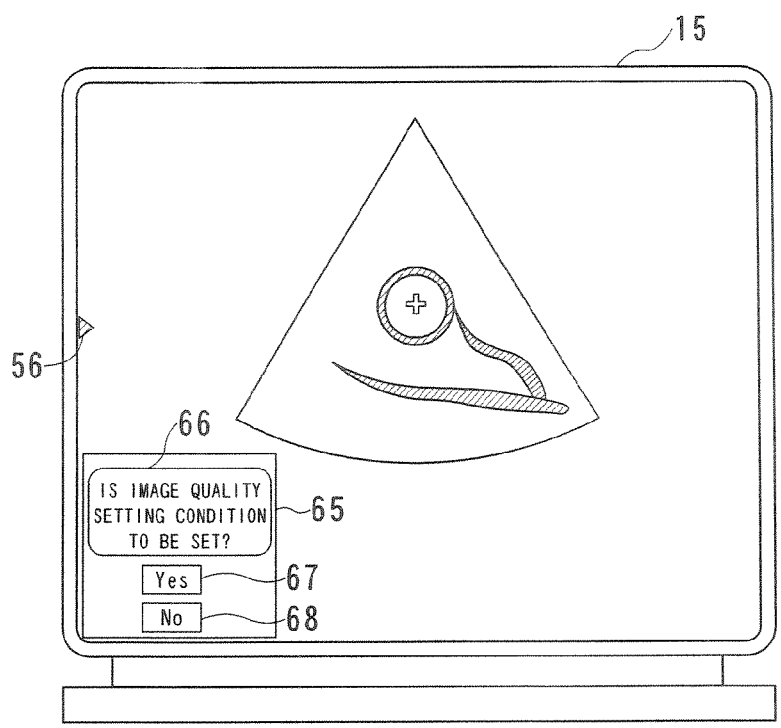
FIG. 20 shows a display example of an image quality setting condition change selection dialog to be displayed on the display unit of FIG. 1.

In Step S99, on the basis of the generated image quality setting condition change selection message dialog display control signal supplied from the control unit 21, the display unit 15 displays an image quality setting condition change selection message dialog 65 shown in FIG. 20.

The image quality setting condition change selection message dialog 65 in FIG. 20 has in addition to the message display column 66, a command display column 67 and a the command display column 68 for displaying a command.

In the case of an example of FIG. 20, the message display column 66 displays a message "image quality setting condition is changed?". As a result, after this process, the operator understands that the image quality setting condition can be changed.

The command display column 67 and the command display column 68 respectively display icons of commands "Yes" and "No". The operator shifts the line-of-sight to shift the pointer 52 displayed on the display unit 15 to the command display column 67 where the icon of the command "Yes" is displayed over the predetermined period of time, thereby selecting the icon of "Yes" of the command display column 67 to cancel the image quality setting condition change process.

Also, the operator shifts the line-of-sight to shift the pointer 52 displayed on the display unit 15 to the command display column 68 shifts the line-of-sight to shift the pointer 52 displayed on the display unit 15 to the command display column is displayed over the predetermined period of time, thereby selecting the icon of "No" of the command display column 68 to instruct the start of the image quality setting condition change process.

In Step S100, the control unit 21 determines whether or not the icon of "Yes" is selected as the operator shifts the line-of-sight to shift the pointer 52 displayed on the display unit 15 over the predetermined period of time on the basis of the image quality setting condition change selection message dialog 65 in FIG. 20.

That is, when the icon of "No" of the command display column 68 is selected as the operator shifts the line-of-sight to shift the pointer 52 displayed on the display unit 15 over the predetermined period of time, in Step S100, the control unit 21 determines that the icon of "Yes" of the command display column 67 is not selected with such a reason that the operator shifts the icon of "Yes" of the command display column 67 to shift the pointer 52 displayed on the display unit 15 over the predetermined period of time. After that, the processes in Step S101 to S104 are skipped and the process proceeds to Step S105, thereby repeatedly performing the processes in Step S105 and thereafter.

On the other hand, when the icon of "Yes" of the command display column 67 is selected as the operator shifts the line-of-sight to shift the pointer 52 displayed on the display unit 15 over the predetermined period of time, in Step S100, the control unit 21 determines that the icon of "Yes" of the command display column 67 is selected with such a reason that the operator shifts the icon of "Yes" of the command display column 67 to shift the pointer 52 displayed on the display unit 15 over the predetermined period of time. After that, the process proceeds to in Step S101.

In this way, the image quality setting condition change selection message dialog 65 is displayed and the operator is caused to choose whether or not the image quality setting condition is changed to the image quality setting condition corresponding to the shifted focal point position with use of its line-of-sight. Thus, the operator can choose whether or not the image quality setting condition is changed according to a preference of the operator. As a result, the operability of the ultrasonic diagnostic apparatus 1 can be improved.

Figure 4:
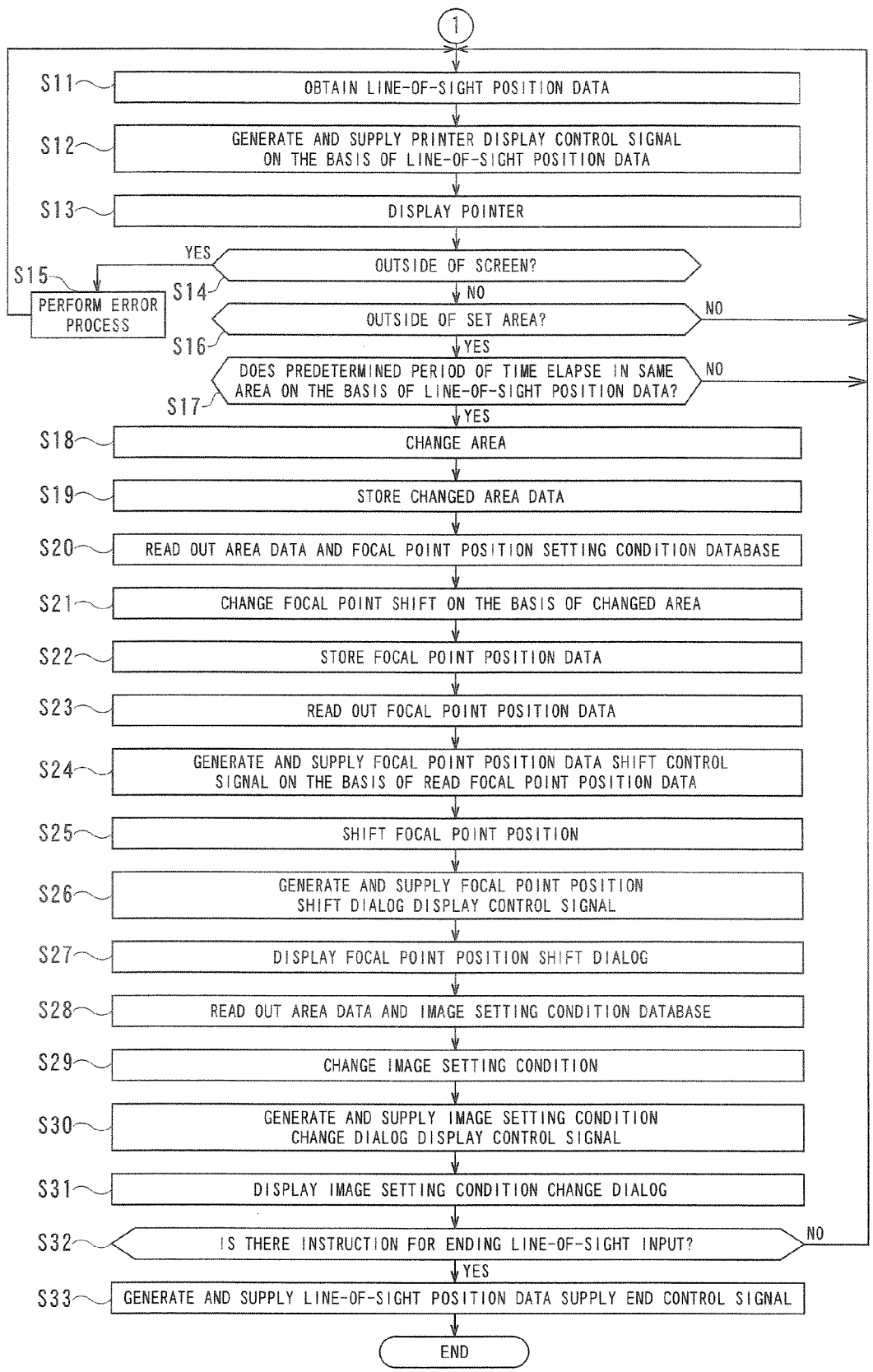
FIG. 4 is a flowchart for describing the line-of-sight input processing of the main body.
Figure 21:
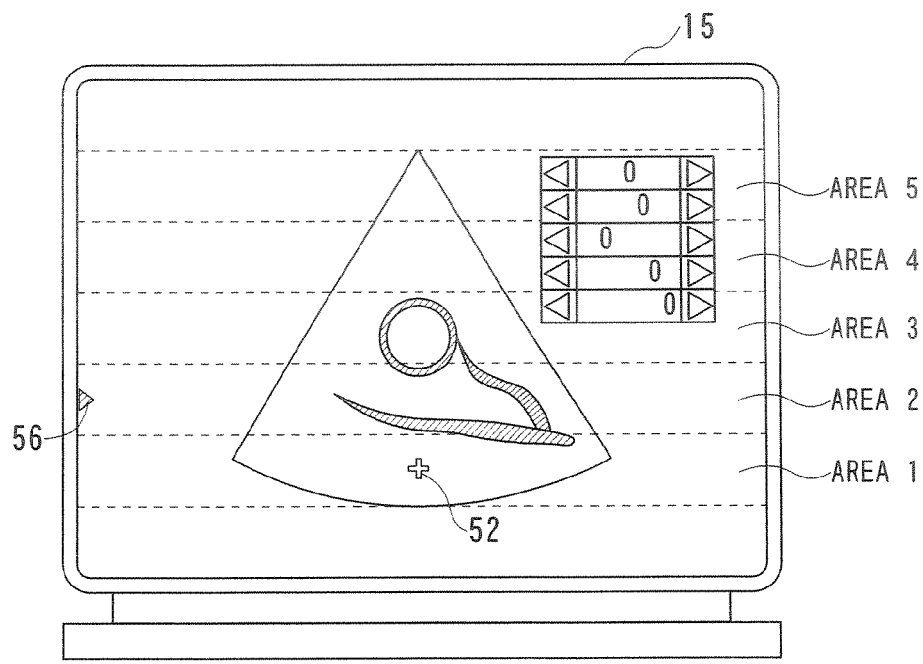
FIG. 21 shows a display example to be displayed on the display unit of FIG. 1.

It should be noted that, for example, through the processes in Step S18 to S29 in FIG. 4, when the focal point position and the image quality setting condition are changed, for example, as shown in FIG. 21, the icons for showing the focal point positions of the respective areas (the areas 1 to 5) are displayed on the display unit 15. When a predetermined period of time elapses (for example, for two seconds) in left and right scroll arrows (operation switch) in which the line-of-sight position of the operator is provided for each area, the focal point position and the image quality setting condition may be changed. As a result, the focal point position can be changed and shifted to the focal point position desired by the operator with higher precision and also the image quality setting condition can be changed to the image quality setting condition optimal in the focal point position. As a result, in general, as compared with other medical diagnostic apparatuses such as an X-ray diagnostic apparatus and X-ray CT apparatus, in the ultrasonic diagnostic apparatus 1 in which the operator has a difficulty of adjusting the image quality, without depending on whether the operator performs a good or bad operation, the performance of the ultrasonic diagnostic apparatus 1 is exerted as much as possible, the image quality of the image displayed on the display unit 15 (for example, the B mode image, the Doppler mode image, or the like) can be further improved.

Therefore, the operability of the ultrasonic diagnostic apparatus 1 can be improved.

Figure 22:
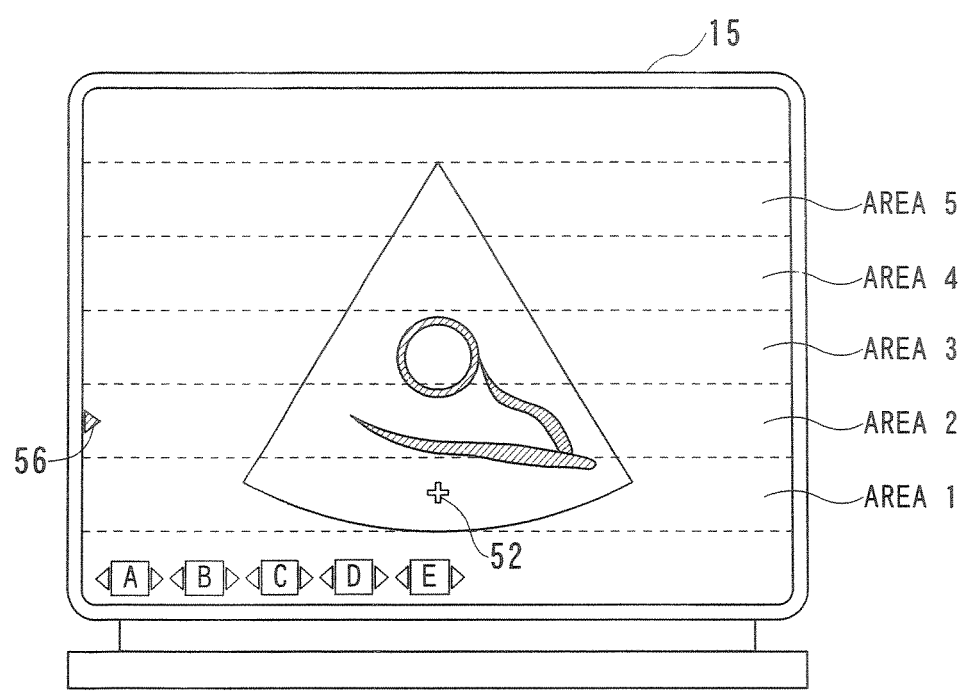
FIG. 22 shows a display example to be displayed on the display unit of FIG. 1.

Then, when the image quality setting condition are changed through the processes in Step S18 to S29 in FIG. 4, for example, as shown in FIG. 22, icons for the respective image quality setting conditions (for example, the transmission waveform of ultrasonic wave, the transmission frequency, the transmission wave number, and the like) are displayed on the display unit 15. As a predetermined period of time (for example, two seconds) elapses in left and right scroll arrows (operation switch) in which the line-of-sight position of the operator is provided for each image quality setting condition, the focal point position and the image quality setting condition may be changed. As a result, the image quality setting condition can be changed to the image quality setting condition optimal in the focal point position desired by the operator.

It should be noted that in the ultrasonic diagnostic apparatus 1 according to the embodiment of the present invention, the line-of-sight position input unit 14 is mounted to the head area of the operator but, for example, the line-of-sight position input unit 14 may be arranged at a part of the upper unit of the screen of the display unit 15 so that the image of the operator can be captured, whereby the line-of-sight position data of the operator is obtained. In the line-of-sight position input unit 14 in this case, only one of the camera 33 and the eye ball camera 34 may be used and, for example, a CCD (Charge Coupled Device) camera may be provided.

In addition, according to the embodiment of the present invention, the line-of-sight position data of the operator is obtained. The focal point position is changed to the focal point position desired by the operator on the basis of the thus obtained line-of-sight position data of the operator. Then, the image quality setting condition is changed to the image quality setting condition optimal in the focal point position. However, for example, head area position data that is data on the head area position of the operator may be obtained with use of a magnetic sensor for detecting a position or an angle of the head area of the operator, the focal point position may be changed to the focal point position desired by the operator on the basis of the thus obtained head area position data of the operator, and the image quality setting condition may be changed to the image quality setting condition optimal in the focal point position. Of course, without the limitation to the line-of-sight or the head area of the operator, any part may be used as long as the part can be obtained as position data.

Furthermore, according to the embodiment of the present invention, "transmission waveform of ultrasonic wave", "transmission frequency", "transmission wave number", "reception frequency", and "acoustic power level of ultrasonic wave" are used as the image quality setting conditions, but "focal point position" registered in the focal point position setting condition database may be used as the image quality setting condition and other than those, for example, conditions such as a transmission/reception filter, the number of scanning lines, an edge enhance process, a gain (in particular, an STC gain (that is, a gain of the TGC circuit) and the like), a dynamic range, and a correlation processing may be used as the image quality setting conditions. Of course, as the image quality setting condition, the above-mentioned conditions can be combined and used in accordance with a purpose.

Also according to the embodiment of the present invention, on the basis of the current line-of-sight position data of the operator, the focal point position is changed to the focal point position desired by the operator, the image quality setting condition is changed to the image quality setting condition optimal in the focal point position but, for example, the setting condition other than the image quality setting condition (for example, a setting condition for performing a process of zooming the screen) is previously registered in a database in association with the line-of-sight position of the operator, its shift, or the like, and on the basis of the current line-of-sight position data of the operator, the setting condition may be changed. For example, when two screens are displayed on the display unit, when the operator shifts the line-of-sight to a predetermined position, a frame rate related to one of the images may be increased relatively. As a result, a preference of the operator during the operation may be reflected. Therefore, the operability of the ultrasonic diagnostic apparatus can be improved.

Of course, the setting condition is previously registered in a database in association with the line-of-sight position of the operator, its shift, or the like, and on the basis of the current line-of-sight position data of the operator, not only the setting condition is changed, but also the display unit 15 is caused to previously display the setting condition, the operation, or the like, so that the operator may issue an instruction with use of the line-of-sight position data of the operator.

Furthermore, according to the embodiment of the present invention, the two dimensional cross-unital image is used but, for example, a three dimensional cross-unital image may be used.

Also, according to the embodiment of the present invention, a cross shaped marker is used as the shape of the pointer 52 displayed on the display unit 15 but, for example, various shapes and colored makers may be used. In addition, before the start of the line-of-sight input process of the main body 11, a desired maker may be previously selected among the plurality of markers by the operator. Moreover, the operator may choose whether or not the pointer 52 is displayed on the display unit 15.

It should be noted that according to the embodiment of the present invention, the area is previously divided into five areas in accordance with the focal point position of the ultrasonic beam at the time of the transmission but the number of areas to be divided may be increased. By increasing the number of areas, more focal point positions desired by the operator can be provided. However, if the number of areas is too many, the focal point position is unnecessarily shifted, so it is necessary to divide the area into an appropriate number to above the unnecessary focal point position shift. As a result, in the focal point position desired by the operator without the unnecessary focal point position shift, the high quality image with higher spatial resolution and high contrast can be displayed.

Then, the series of processes described in the embodiment of the present invention can be executed by a software as well as a hardware.

Furthermore, according to the embodiment of the present invention, for the steps in the flowcharts, the example in which the processes are executed in the stated order in a time oriented manner has been described, but an example in which the processes are executed in parallel or individually executed while not necessarily executed in the time oriented manner may also be included in the steps.

What is claimed is:

1. An ultrasonic diagnostic apparatus, comprising:
   an image data obtaining unit configured to make an ultrasonic probe transmit ultrasonic waves to a subject and receive reflected waves, and to obtain image data based on the reflected waves and to generate and ultrasonic image based on the obtained image data;
   a dividing unit configured to divide an ultrasonic image, based on the image data, to be displayed on a display into a plurality of division areas;
   a line-of-sight position data obtaining unit configured to obtain line-of-sight position data that is data on a line-of-sight position of an operator;
   a control unit configured to determine a division area related to the line-of-sight position data from the division areas;
   a setting condition change unit configured to change a setting condition for obtaining the image data by the image obtaining unit in accordance with the determined division area; and
   a time determination unit configured to determine whether or not the line-of-sight position of the operator belongs to a same division area for a predetermined period of time based on the line-of-sight position data obtained by the line-of-sight position data obtaining unit, wherein when it is determined that the line-of-sight position of the operator belongs to the same division area for the predetermined period of time by the time determination unit, the setting condition change unit changes the division area to which the current line-of-sight position of the operator belongs, from a predetermined division area that has been previously set, to the division area to which the line-of-sight position of the operator belongs for the predetermined period of time which is determined by the time determination unit, and changes the setting condition based on the changed division area.

2. The ultrasonic diagnostic apparatus according to claim 1, wherein the setting condition changed by the setting condition change unit at least includes a focal point position of the ultrasonic waves transmitted.

3. The ultrasonic diagnostic apparatus according to claim 2, wherein the setting condition change unit changes the focal point position as the setting condition so that the focal point position is a position within the subject, which relates to the determined division area.

4. The ultrasonic diagnostic apparatus according to claim 2, further comprising:
   a display control unit configured to display, on the display, the ultrasonic image and indicating different focal point positions of the ultrasonic waves, and to display a current focal point position in the image data and a pointer indicating a current line-of-sight of the operator.

5. The ultrasonic diagnostic apparatus according to claim 1, wherein the setting condition changed by the setting condition change unit includes at least one of a transmission waveform of the ultrasonic wave, a transmission frequency of the ultrasonic wave, a transmission wave number of the ultrasonic wave, a reception frequency of the ultrasonic wave, an acoustic power level of the ultrasonic wave, a gain of the ultrasonic wave, and a dynamic range of the ultrasonic wave.

6. The ultrasonic diagnostic apparatus according to claim 1, wherein the setting condition changed by the setting condition change unit is an image quality setting condition related to an image quality of the image data that is obtained by the image data obtaining unit.

7. The ultrasonic diagnostic apparatus according to claim 1, further comprising:
a line-of-sight input start instruction determination unit configured to determine whether or not there is an instruction on starting a line-of-sight input; and
a line-of-sight input end instruction determination unit configured to determine whether or not there is an instruction on ending the line-of-sight input, wherein
the line-of-sight position data obtaining unit starts obtaining the line-of-sight position data when it is determined by the line-of-sight input start instruction determination unit that there is an instruction on starting the line-of-sight input, and repeats the obtaining of the line-of-sight position data until the line-of-sight input end instruction determination unit determines that there is an instruction on ending the line-of-sight input.

8. The ultrasonic diagnostic apparatus according to claim 1, further comprising:
a display control unit configured to display, on the display, one of a drawing represented by an icon indicating that the setting condition is changed, a text, and a dialog when the setting condition is changed by the setting condition change unit.

9. The ultrasonic diagnostic apparatus according to claim 1, further comprising:
a selection reception unit configured to receive a selection indicating whether or not the setting condition is changed by the setting condition change unit, wherein the setting condition change unit changes the setting condition when the selection reception unit receives the selection of changing the setting condition.

10. The ultrasonic diagnostic apparatus according to claim 1, further comprising:
an image capturing unit configured to capture an image of eyeballs of the operator, wherein the line-of-sight position data obtaining unit obtains the line-of-sight position data based on the image of the eyeballs.

11. The ultrasonic diagnostic apparatus according to claim 1, wherein the dividing unit divides the ultrasonic image into the plurality of division areas in a vertical direction.

12. The ultrasonic diagnostic apparatus according to claim 1, further comprising:
a display control unit configured to display, on the display, the ultrasonic images based on the image data obtained by different setting conditions.

13. An ultrasonic diagnostic method, comprising:
making an ultrasonic probe transmit ultrasonic waves to a subject and receiving reflected waves, and obtaining image data based on the reflected waves;
generating an ultrasonic image based on the image data;
dividing the ultrasonic image, based on the image data, to be displayed on a display into five division areas in accordance with the focal point position of the ultrasonic beam at the time of transmission;
obtaining line-of-sight position data that is data on a line-of-sight position of an operator, generating a pointer, based on the obtained line of sight position data, and displaying the pointer on the display such that the operator can find out where its own line-of-sight position exists of the screen of the display within the five division areas of the display;
determining which division area is the line-of-sight position data located, based on the location of the pointer, within the division areas;
changing at least one setting condition, including a focal point position of the ultrasonic waves, for obtaining the image data by the ultrasonic probe in accordance with the determined division area in where the line-of-sight position is located; and,
determining whether or not the line-of-sight position of the operator belongs to a same division area for a predetermined period of time based on the line-of-sight position data, wherein when it is determined that the line-of-sight position of the operator belongs to the same division area for the predetermined period of time, the division area to which the current line-of-sight position of the operator belongs is changed, from a predetermined division area that has been previously set, to the division area to which the line-of-sight position of the operator belongs for the predetermined period of, and further changes the at least one setting condition based on the changed division area.

14. A non-transitory computer-readable storage medium encoded with a computer readable program configured to cause an information processing apparatus to execute a method, the method comprising:
making an ultrasonic probe transmit ultrasonic waves to a subject and receiving reflected waves, and obtaining image data based on the reflected waves;
generating an ultrasonic image based on the image data;
dividing the ultrasonic image, based on the image data, to be displayed on a display into five division areas in accordance with the focal point position of the ultrasonic beam at the time of transmission;
obtaining line-of-sight position data that is data on a line-of-sight position of an operator, generating a pointer, based on the obtained line of sight position data, and displaying the pointer on the display such that the operator can find out where its own line-of-sight position exists of the screen of the display within the five division areas of the display;
determining a which division area is the line-of-sight position data located, based on the location of the pointer, within the division areas;
changing at least one setting condition, including a focal point position of the ultrasonic waves, for obtaining the image data by the ultrasonic probe in accordance with the determined division area in where the line-of-sight position is located; and,
determining whether or not the line-of-sight position of the operator belongs to a same division area for a predetermined period of time based on the line-of-sight position data, wherein when it is determined that the line-of-sight position of the operator belongs to the same division area for the predetermined period of time, the division area to which the current line-of-sight position of the operator belongs is changed, from a predetermined division area that has been previously set, to the division area to which the line-of-sight position of the operator belongs for the predetermined period of, and further changes the at least one setting condition based on the changed division area.

* * * * *